(12) United States Patent
Shaw et al.

(10) Patent No.: US 12,071,666 B2
(45) Date of Patent: Aug. 27, 2024

(54) HUMAN GENETIC MARKERS ASSOCIATED WITH RESPONSE TO TREATMENTS THAT TARGET CLOSTRIDIUM DIFFICILE TOXIN B

(71) Applicants: Merck Sharp & Dohme LLC, Rahway, NJ (US); Beijing Genomics Institute at Shenzhen, Guangdong (CN)

(72) Inventors: Peter M. Shaw, Yardley, PA (US); Devan V. Mehrotra, Lansdale, PA (US); Rebecca L. Blanchard, Allentown, PA (US); Judong Shen, Westfield, NJ (US); Robin Mogg, Chalfont, PA (US); Mary Beth Dorr, Collegeville, PA (US); Junhua Li, Shenzhen (CN); Xun Xu, Shenzhen (CN)

(73) Assignees: Merck Sharp & Dohme LLC, Rahway, NJ (US); Beijing Genomics Institute at Shenzhen, Shenzhen (CN)

( * ) Notice: Subject to any disclaimer, the term of this patent is extended or adjusted under 35 U.S.C. 154(b) by 80 days.

(21) Appl. No.: 16/468,982

(22) PCT Filed: Dec. 7, 2017

(86) PCT No.: PCT/US2017/064985
§ 371 (c)(1),
(2) Date: Jun. 12, 2019

(87) PCT Pub. No.: WO2018/111662
PCT Pub. Date: Jun. 21, 2018

(65) Prior Publication Data
US 2020/0017909 A1 Jan. 16, 2020

Related U.S. Application Data

(60) Provisional application No. 62/508,066, filed on May 18, 2017.

(30) Foreign Application Priority Data

Dec. 14, 2016 (WO) ............... PCT/CN2016/109900

(51) Int. Cl.
| | | |
|---|---|---|
| *C12Q 1/6876* | (2018.01) | |
| *A61K 31/4164* | (2006.01) | |
| *A61K 31/7048* | (2006.01) | |
| *A61K 38/14* | (2006.01) | |
| *A61K 39/40* | (2006.01) | |
| *A61P 31/04* | (2006.01) | |
| *C07K 16/12* | (2006.01) | |

(52) U.S. Cl.
CPC ........ *C12Q 1/6876* (2013.01); *A61K 31/4164* (2013.01); *A61K 31/7048* (2013.01); *A61K 38/14* (2013.01); *A61K 39/40* (2013.01); *A61P 31/04* (2018.01); *C07K 16/1282* (2013.01); *C07K 2317/565* (2013.01); *C12Q 2600/106* (2013.01); *C12Q 2600/156* (2013.01)

(58) Field of Classification Search
CPC ...... A61K 39/00; A61K 39/02; A61K 39/395; A61K 49/00
USPC ..... 424/9.1, 9.2, 130.1, 164.1, 167.1, 234.1, 424/236.1, 239.1
See application file for complete search history.

(56) References Cited

U.S. PATENT DOCUMENTS

| | | | |
|---|---|---|---|
| 9,181,632 B1 * | 11/2015 | Murgolo | ............... C12N 9/1051 |
| 9,364,542 B2 | 6/2016 | Chang | |
| 2010/0035265 A1 | 2/2010 | Floratos et al. | |
| 2012/0156200 A1 | 6/2012 | Nan et al. | |
| 2014/0348844 A1 * | 11/2014 | Humphreys | ........... A61K 39/40 424/139.1 |
| 2015/0344940 A1 * | 12/2015 | Savidge | ............... C12Q 1/6883 424/93.41 |

FOREIGN PATENT DOCUMENTS

| | | | |
|---|---|---|---|
| WO | WO-2008118469 A2 * | 10/2008 | ............. C12Q 1/703 |
| WO | WO2010050829 A1 | 5/2010 | |
| WO | WO2016193136 A1 | 12/2016 | |
| WO | 2018/107388 A1 | 6/2018 | |

OTHER PUBLICATIONS

Lowy et al. (The New England Journal of Medicine, 362(3): 197-205, Jan. 21, 2010).*
Of He et al. Nature Genetics vol. 43, No. 1, 2015 . WO2008118469A2. (Year: 2015).*
Sambol et al. Infection and Immunity, vol. 68, No. 10, pp. 5450-5457 Oct. 2000 (Year: 2000).*
Bartlett et al., The Case for Vancomycin as the Preferred Drug for Treatment of Clostridium difficile Infection, Clinical Infectious Diseases, 2008, 1489-92, 46(10).

(Continued)

*Primary Examiner* — Jana A Hines
*Assistant Examiner* — Khatol S Shahnan Shah
(74) *Attorney, Agent, or Firm* — Arnold & Porter Kaye Scholer LLP

(57) ABSTRACT

The present invention provides genetic markers on human chromosome 6 that are associated with a beneficial response to a treatment that targets *Clostridium difficile* (*C. difficile*) toxin B (TcdB), e.g. a TcdB antibody. These TcdB treatment response markers are useful, inter alia, to identify patients who are most likely to benefit from treatment that targets TcdB in methods of treating patients having a disease susceptible to treatment with a TcdB antibody, and in methods for selecting the most appropriate therapy for such patients. The invention also provides antibodies, drug products, and kits useful with the TcdB Treatment response markers of the invention.

30 Claims, 13 Drawing Sheets

Specification includes a Sequence Listing.

(56) References Cited

OTHER PUBLICATIONS

Bauer et al., Clostridium difficile infection in Europe: a hospital-based survey, Lancet, 2011, 63-73, 377(9759).
Bouza, Emilio, et al., Antimicrobial Therapy of Clostridium difficile-Associated Diarrhea, The Medical Clinics of North America, 2006, p. 1141-1163, vol. 90.
Dupont et al., New advances in Clostridium difficile infection: changing epidemiology, diagnosis, treatment and control, Current Opinion in Infectious Diseases, 2008, 500-507, 21.
Gorbach, S.L., Antibiotics and Clostridium Difficile, The New England Journal of Medicine, 1999, 1690-1691, 341(22).
He et al., Emergence and global spread of epidemic healthcare-associated Clostridium difficile, Nature genetics, 2013, pp. 109-113, vol. 45(1).
Hjelm, Lawrence, N. et al., A Simple Method to Confirm and Size Deletion, Duplication, and Insertion Mutations Detected by Sequence Analysis, Journal of Molecular Diagnostics, 2010, p. 607-610, vol. 12, No. 5.
Howie, Bryan, et al., Fast and accurate genotype imputation in genome-wide association studies through pre-phasing, Nature Genetics, 2012, p. 955-959, vol. 44, No. 8.
Kelly et al., Clostridium Difficile Colitis, The New England Journal of Medicine, 1994, 257-262, 330(4).
Lessa, et al., Burden of Clostridium difficile Infection in the United States, The New England Journal of Medicine, 2015, p. 825-834, vol. 372, No. 9.
Mcfarland, Lynee, V., Renewed interest in a difficult disease: Clostridium difficile infections—epidemiology and current treatment strategies, Current Opinion in Gastroenterology, 2008, p. 24-35, vol. 25.
Price, Alkes, L. et al., Principal components analysis corrects for stratification in genome-wide association studies, Nature Genetics, 2006, p. 904-909, vol. 38, No. 8.
Shaw et al., Genome Wide Analysis Reveals Host Genetic Variants that Associate with Reduction in Clostridium difficile infection Recurrence (rCDI) in Patients Treated with Bezlotoxumab, Open Forum Infect Dis., 2017, pp. S380, vol. 4, Suppl. 1.
SNNP ID: TSC0014496—Sep. 19, 2002.
Zheng, X. et al., HIBAG-HLA genotype imputation with attribute bagging, The Pharmacogenomics Journal, 2014, p. 192-200, vol. 14.
Anonymous, "Prescribing Information for Zinplava," retrieved from the internet at accessdata(dot)fda(dot)gov/drugsatfda_docs/label/2016/761046s001b1.pdf, pp. 1-11 (Oct. 1, 2016).
Anonymous, "ss114142737 (rs2516513)," retrieved from the internet at ncbi(dot)nlm(dot)nih(dot)gov/projects/SNP/nsp_ss(dot)cgi?subsnp_id=22114142737, p. 1 (Mar. 29, 2010)
International Search Report dated Sep. 14, 2017, in PCT/CN2016/109900.
International Search Report dated May 1, 2018, in PCT/CN2017/064985.
Shen et al., "Genetic Association Reveals Protection Against Recurrence of Clostridium difficile Infection with Bezlotoxumab Treatment," *American Society for Microbiology*, 5(3):1-13 (2020).
De La Vega et al., "The Linkage Disequilibrium Maps of Three Human Chromosomes Across Four Populations Reflect the Demographic History and a Common Underlying Recombination Pattern," *Genome Research*, 15:454-462 (2005).
Extended European Search Report, issued May 28, 2020, in European Application 17881986.8.
Hernandez et al., "Broad Coverage of Genetically Diverse Strains of *Clostridium difficile* by Actoxumab and Bezlotoxumab Predicted by In Vitro Neutralization and Epitope Modeling," 59(2):1052-1060 (Feb. 2015).
Hill et al., "Linkage Disequilibrium in Finite Populations," *Theoretical and Applied Genetics*, 38:226-231 (1968).
Laan et al., "Demographic History and Linkage Disequilibrium in Human Populations," *Nature Genetics*, 17:435-438 (1997).
Shifman et al., "Linkage Disequilibrium Patterns of the Human Genome Across Populations," *Human Molecular Genetics*, 12(7):771-776 (2003).
Warn et al., "Disease Progression and Resolution in Rodent Models of Clostridium difficile Infection and Impact of Antitoxin Antibodies and Vancomycin," *Antimicrobial Agents and Chemotherapy*, 60(11):6471-6482 (2016).

\* cited by examiner

Proportion of subjects with CDI recurrence

| Treatment | %(n/N) | Treatment vs. Placebo | | |
|---|---|---|---|---|
| | | Unadjusted Difference | Adjusted Difference (95% CI)† | p-Value† |
| MK-3415A | 15.4 (119/773) | -11.3 | -11.2 (-15.2, -7.2) | <0.0001 |
| MK-6072 | 16.5 (129/781) | -10.1 | -10.0 (-14.0, -6.0) | <0.0001 |
| Placebo | 26.6 (206/773) | --- | --- | --- |

Pairwise Comparisons

| Comparison of Active Treatment Groups | Unadjusted Difference | Adjusted Difference (95% CI)† | p-Value† |
|---|---|---|---|
| MK-3415A vs. MK-6072 | -1.1 | -1.1 (-4.8, 2.5) | 0.2726 |

† One sided p-value based on the Miettinen and Nurminen method stratified by protocol (P001 vs P002), SoC therapy (metronidazole vs. vancomycin vs. fidaxomicin) and hospitalization status (inpatient vs. outpatient)
n = Number of subjects in the analysis population meeting the criteria for endpoint.
N = Number of subjects included in the analysis population.
SoC = Standard of Care, MK-3415A = actoxumab + bezlotoxumab, MK-6072 = bezlotoxumab alone

FIG.2

CDI Recurrence by Subgroup

| Subjects in population | PN001 + PN002 | | Difference (95%CI)[1] |
|---|---|---|---|
| | MK-6072 N=781 % (n/m) | Placebo N=773 % (n/m) | |
| ≥65 years of age | 15.4 (60/390) | 31.4 (127/405) | −16.0 (−21.7, −10.2) |
| History of CDI in past 6 months | 25.0 (54/216) | 41.1 (90/219) | −16.1 (−24.7, −7.3) |
| Clinically Severe CDI | 10.7 (13/122) | 22.4 (28/125) | −11.7 (−21.1, −2.5) |
| 027 Ribotype | 24.4 (21/86) | 34.0 (32/94) | −9.6 (−22.6, 3.8) |
| Epidemic strain[2] | 21.3 (44/207) | 32.3 (73/226) | −11.0 (−19.2, −2.7) |
| Compromised Immunity | 15.4 (26/169) | 28.3 (41/145) | −12.9 (−22.1, −3.8) |

CI=Confidence interval
CDI= *Clostridium difficile* infection
Data in cells: %(n/m) where m = Number of subjects within subgroup and n = Number of subjects within subgroup that met the criteria for endpoint.
[1] Based on the Mieffinen and Nurminen method without stratification
[2] Epidemic strain includes the following: 027, 014, 002, 001, 106, or 020 ribotypes

FIG.3

Subjects with CDI Recurrence in Treatment Arms of PN001 and PN002

| GWAS data sets used for analysis | Treatment arm | Overall population, FAS | | | Subject with genetic consent used in genetic analysis population within FAS | |
|---|---|---|---|---|---|---|
| | | PN001 %, (n/N) | PN002 %, (n/N) | | PN001 %, (n/N) | PN002 %, (n/N) |
| Used and Pooled | MK-6072 and MK-3415 | 15.9 (61/383) | 14.9 (58/390) | | 16.1 (26/161) | 16.8 (24/143) |
| | MK-6072 | 17.4 (67/386) | 15.7 (62/395) | | 21.1 (36/170) | 17.3 (23/133) |
| | Placebo | 27.6 (109/395) | 25.7 (97/378) | | 30.4 (51/168) | 25.4 (31/122) |
| Used | MK-3415 | 25.9 (60/232) | | | 28.8 (30/104) | |
| Not Used | | | | | | |
| Total in different studies | | 21.3 (297/1396) | 18.7 (217/1163) | | 23.7 (143/603) | 19.6 (78/398) |

▨ Subjects with genetic consent from MK-6072 containing arms were pooled for GWAS analysis
▥ Subjects with genetic consent from placebo containing arms were pooled for GWAS analysis

FIG.4

| SNPs in LD with rs2516513 SNP ||||||| 
|---|---|---|---|---|---|---|
| CHR_A | BP_A | SNP_A | CHR_B | BP_B | SNP_B | $r^2$ |
| 6 | 31447588 | rs2516513 | 6 | 31447588 | rs2516513 | 1 |
| 6 | 31447588 | rs2516513 | 6 | 31449269 | rs2516422 | 0.994579 |
| 6 | 31447588 | rs2516513 | 6 | 31448625 | rs2516511 | 0.994577 |
| 6 | 31447588 | rs2516513 | 6 | 31451680 | rs2523705 | 0.994552 |
| 6 | 31447588 | rs2516513 | 6 | 31449994 | rs2516509 | 0.991884 |
| 6 | 31447588 | rs2516513 | 6 | 31446796 | rs2248462 | 0.986462 |
| 6 | 31447588 | rs2516513 | 6 | 31446466 | rs2248372 | 0.524532 |
| 6 | 31447588 | rs2516513 | 6 | 31472459 | rs2534657 | 0.50733 |
| 6 | 31447588 | rs2516513 | 6 | 31465899 | rs2516498 | 0.504465 |

FIG.5A

SNPs in LD with rs113379306 SNP

| CHR_A | BP_A | SNP_A | CHR_B | BP_B | SNP_B | $r^2$ |
|---|---|---|---|---|---|---|
| 6 | 17333351 | rs113379306 | 6 | 17333351 | rs113379306 | 1 |
| 6 | 17333351 | rs113379306 | 6 | 17329940 | rs76166871 | 0.986935 |
| 6 | 17333351 | rs113379306 | 6 | 17329054 | rs144055871 | 0.986789 |
| 6 | 17333351 | rs113379306 | 6 | 17331186 | rs113772197 | 0.949081 |
| 6 | 17333351 | rs113379306 | 6 | 17331658 | rs112655105 | 0.949081 |
| 6 | 17333351 | rs113379306 | 6 | 17331679 | rs111346228 | 0.949081 |
| 6 | 17333351 | rs113379306 | 6 | 17333517 | rs143709219 | 0.852999 |
| 6 | 17333351 | rs113379306 | 6 | 17335499 | rs112077510 | 0.852999 |
| 6 | 17333351 | rs113379306 | 6 | 17338435 | rs75811245 | 0.852999 |
| 6 | 17333351 | rs113379306 | 6 | 17338526 | rs111820636 | 0.852999 |
| 6 | 17333351 | rs113379306 | 6 | 17338808 | rs112024681 | 0.852999 |
| 6 | 17333351 | rs113379306 | 6 | 17338848 | rs112177523 | 0.852999 |
| 6 | 17333351 | rs113379306 | 6 | 17342235 | rs113930107 | 0.852999 |
| 6 | 17333351 | rs113379306 | 6 | 17355188 | rs74739069 | 0.843323 |
| 6 | 17333351 | rs113379306 | 6 | 17362236 | rs79118185 | 0.843323 |
| 6 | 17333351 | rs113379306 | 6 | 17364561 | rs113935953 | 0.843323 |
| 6 | 17333351 | rs113379306 | 6 | 17374276 | rs115793598 | 0.843323 |
| 6 | 17333351 | rs113379306 | 6 | 17381830 | rs149305651 | 0.843323 |
| 6 | 17333351 | rs113379306 | 6 | 17357005 | rs111917165 | 0.797791 |
| 6 | 17333351 | rs113379306 | 6 | 17350645 | rs112462317 | 0.789215 |
| 6 | 17333351 | rs113379306 | 6 | 17360387 | rs3929906 | 0.756529 |
| 6 | 17333351 | rs113379306 | 6 | 17361495 | rs113049715 | 0.756529 |
| 6 | 17333351 | rs113379306 | 6 | 17361784 | rs113869594 | 0.756529 |
| 6 | 17333351 | rs113379306 | 6 | 17366852 | rs75397691 | 0.697944 |
| 6 | 17333351 | rs113379306 | 6 | 17368491 | rs6915437 | 0.697944 |
| 6 | 17333351 | rs113379306 | 6 | 17369575 | rs75577118 | 0.697944 |
| 6 | 17333351 | rs113379306 | 6 | 17377697 | rs142577109 | 0.697944 |
| 6 | 17333351 | rs113379306 | 6 | 17365580 | rs111737868 | 0.647143 |
| 6 | 17333351 | rs113379306 | 6 | 17365929 | rs111714094 | 0.647143 |
| 6 | 17333351 | rs113379306 | 6 | 17366938 | rs139208445 | 0.647143 |
| 6 | 17333351 | rs113379306 | 6 | 17369316 | rs79986229 | 0.647143 |
| 6 | 17333351 | rs113379306 | 6 | 17372882 | rs112198251 | 0.647143 |
| 6 | 17333351 | rs113379306 | 6 | 17374574 | rs112623467 | 0.647143 |
| 6 | 17333351 | rs113379306 | 6 | 17376320 | rs150847039 | 0.647143 |
| 6 | 17333351 | rs113379306 | 6 | 17325391 | rs74348921 | 0.64418 |
| 6 | 17333351 | rs113379306 | 6 | 17327182 | rs72833643 | 0.641383 |
| 6 | 17333351 | rs113379306 | 6 | 17373351 | rs77084289 | 0.635538 |
| 6 | 17333351 | rs113379306 | 6 | 17374638 | rs112152743 | 0.635414 |
| 6 | 17333351 | rs113379306 | 6 | 17324101 | rs113577849 | 0.603931 |
| 6 | 17333351 | rs113379306 | 6 | 17322876 | rs112470701 | 0.598176 |
| 6 | 17333351 | rs113379306 | 6 | 17380313 | rs113289671 | 0.540171 |
| 6 | 17333351 | rs113379306 | 6 | 17381638 | rs73365901 | 0.531699 |
| 6 | 17333351 | rs113379306 | 6 | 17382242 | rs7770541 | 0.527496 |

FIG.5B

SNPs in LD with rs76166871 SNP

| CHR_A | BP_A | SNP_A | CHR_B | BP_B | SNP_B | $r^2$ |
|---|---|---|---|---|---|---|
| 6 | 17329940 | rs76166871 | 6 | 17329054 | rs144055871 | 1 |
| 6 | 17329940 | rs76166871 | 6 | 17329940 | rs76166871 | 1 |
| 6 | 17329940 | rs76166871 | 6 | 17333351 | rs113379306 | 0.986935 |
| 6 | 17329940 | rs76166871 | 6 | 17331186 | rs113772197 | 0.961728 |
| 6 | 17329940 | rs76166871 | 6 | 17331658 | rs112655105 | 0.961728 |
| 6 | 17329940 | rs76166871 | 6 | 17331679 | rs111346228 | 0.961728 |
| 6 | 17329940 | rs76166871 | 6 | 17333517 | rs143709219 | 0.841862 |
| 6 | 17329940 | rs76166871 | 6 | 17335499 | rs112077510 | 0.841862 |
| 6 | 17329940 | rs76166871 | 6 | 17338435 | rs75811245 | 0.841862 |
| 6 | 17329940 | rs76166871 | 6 | 17338526 | rs111820636 | 0.841862 |
| 6 | 17329940 | rs76166871 | 6 | 17338808 | rs112024681 | 0.841862 |
| 6 | 17329940 | rs76166871 | 6 | 17338848 | rs112177523 | 0.841862 |
| 6 | 17329940 | rs76166871 | 6 | 17342235 | rs113930107 | 0.841862 |
| 6 | 17329940 | rs76166871 | 6 | 17355188 | rs74739069 | 0.832314 |
| 6 | 17329940 | rs76166871 | 6 | 17362236 | rs79118185 | 0.832314 |
| 6 | 17329940 | rs76166871 | 6 | 17364561 | rs113935953 | 0.832314 |
| 6 | 17329940 | rs76166871 | 6 | 17374276 | rs115793598 | 0.832314 |
| 6 | 17329940 | rs76166871 | 6 | 17381830 | rs149305651 | 0.832314 |
| 6 | 17329940 | rs76166871 | 6 | 17357005 | rs111917165 | 0.787378 |
| 6 | 17329940 | rs76166871 | 6 | 17350645 | rs112462317 | 0.778915 |
| 6 | 17329940 | rs76166871 | 6 | 17360387 | rs3929906 | 0.746656 |
| 6 | 17329940 | rs76166871 | 6 | 17361495 | rs113049715 | 0.746656 |
| 6 | 17329940 | rs76166871 | 6 | 17361784 | rs113869594 | 0.746656 |
| 6 | 17329940 | rs76166871 | 6 | 17366852 | rs75397691 | 0.68884 |
| 6 | 17329940 | rs76166871 | 6 | 17368491 | rs6915437 | 0.68884 |
| 6 | 17329940 | rs76166871 | 6 | 17369575 | rs75577118 | 0.68884 |
| 6 | 17329940 | rs76166871 | 6 | 17377697 | rs142577109 | 0.68884 |
| 6 | 17329940 | rs76166871 | 6 | 17325391 | rs74348921 | 0.652892 |
| 6 | 17329940 | rs76166871 | 6 | 17327182 | rs72833643 | 0.650264 |
| 6 | 17329940 | rs76166871 | 6 | 17365580 | rs111737868 | 0.638704 |
| 6 | 17329940 | rs76166871 | 6 | 17365929 | rs111714094 | 0.638704 |
| 6 | 17329940 | rs76166871 | 6 | 17366938 | rs139208445 | 0.638704 |
| 6 | 17329940 | rs76166871 | 6 | 17369316 | rs79986229 | 0.638704 |
| 6 | 17329940 | rs76166871 | 6 | 17372882 | rs112198251 | 0.638704 |
| 6 | 17329940 | rs76166871 | 6 | 17374574 | rs112623467 | 0.638704 |
| 6 | 17329940 | rs76166871 | 6 | 17376320 | rs150847039 | 0.638704 |
| 6 | 17329940 | rs76166871 | 6 | 17374638 | rs112152743 | 0.627129 |
| 6 | 17329940 | rs76166871 | 6 | 17373351 | rs77084289 | 0.62704 |
| 6 | 17329940 | rs76166871 | 6 | 17324101 | rs113577849 | 0.612385 |
| 6 | 17329940 | rs76166871 | 6 | 17322876 | rs112470701 | 0.606231 |
| 6 | 17329940 | rs76166871 | 6 | 17380313 | rs113289671 | 0.533134 |
| 6 | 17329940 | rs76166871 | 6 | 17381638 | rs73365901 | 0.524772 |
| 6 | 17329940 | rs76166871 | 6 | 17382242 | rs7770541 | 0.520625 |

FIG.5C

HUMAN GENETIC MARKERS ASSOCIATED WITH RESPONSE TO TREATMENTS THAT TARGET CLOSTRIDIUM DIFFICILE TOXIN B

CROSS-REFERENCE TO RELATED APPLICATIONS

This application is a § 371 National Stage Application of PCT/US2017/064985, international filing date of Dec. 7, 2017, which claims the benefit of U.S. Provisional Application Ser. No. 62/508,066, filed May 18, 2017, and International Application No. PCT/CN16/109900, filed Dec. 14, 2016, expired.

FIELD OF THE INVENTION

The present invention relates to genetic markers on human chromosome 6 that are predictive of a beneficial response to treatment with molecules that target *C. difficile* toxin B in a patient in need thereof. The invention also provides methods of using the genetic markers for the diagnosis and/or treatment of said patients.

REFERENCE TO SEQUENCE LISTING SUBMITTED ELECTRONICALLY

The sequence listing of the present application is submitted electronically via EFS-Web as an ASCII formatted sequence listing with a file name "24383USPCT-SEQLIST-12JUNE2019.TXT," creation date of Jun. 12, 2019, and a size of 7.8 KB. This sequence listing submitted via EFS-Web is part of the specification and is herein incorporated by reference in its entirety.

BACKGROUND OF THE INVENTION

*Clostridium difficile* (*C. difficile*), an anaerobic, spore forming, gram-positive *bacillus*, is the most common cause of health care acquired infections in the United States (U.S.) and Europe (Lessa et al., "Burden of *Clostridium difficile* infection in the United States," N Engl J Med., 2015, 372(9):825-34). The U.S. Centers for Disease Control (CDC) has declared *C. difficile* an urgent public health threat (Center for Disease Control and Prevention. Antibiotic resistance threats in the United States, 2013. Atlanta, GA: U.S., Department of Health and Human Services). According to the CDC, it is estimated that in 2011 *C. difficile* was responsible for almost half a million infections, including 453,000 estimated *C. difficile* infection (CDI) cases in the U.S., and an additional 83,000 recurrent cases (Lessa et al., supra). CDI was also associated with approximately 29,000 deaths (Lessa et al., 2015, supra). European studies report similar estimates of CDI recurrence rate (Bauer et al., "*Clostridium difficile* infection in Europe: a hospital-based survey," Lancet, 2011, 377:63-73).

Almost all antibiotics, including clindamycin, cephalosporins, penicillins, and fluoroquinolones, have been associated with symptomatic disease caused by toxigenic *C. difficile* (Bartlett, J. G., Clin Infect Dis. 46(10): 1489-92 (2008); Gorbach, S. L., N Engl J Med, 341(22): 1690-1 (1999); Kelly et al., N Engl J Med 330(4): 257-62 (1994)). *C. difficile*-associated disease includes antibiotic-associated diarrhea, colitis and pseudomembranous colitis and in some cases, may progress to toxic megacolon, sepsis and death. Although some patients suffering from CDI respond to cessation of antibiotic therapy, most require treatment with further agents, such as metronidazole or vancomycin (reviewed in DuPont et al., Current Opinion in Infectious Diseases 21:500-507 (2008)). Existing therapies often fail to eliminate CDI or lead to recurrent illness; thus, new methods of prophylactic or therapeutic treatment are needed.

One of the greatest challenges in managing CDI is preventing recurrence. Following a successful treatment of initial CDI, between 15% and 35% of patients develop recurrence (Bouza et al., Antimicrobial therapy of *Clostridium difficile*-associated diarrhea. Med Clin N Am 2006; 90: 1141-63; McFarland L V. Renewed interest in a difficult disease: *Clostridium difficile* infections-epidemiology and current treatment strategies. Curr Opin Gastroenterol. 2009, 25(1): 24-35). The majority of these recurrences occur within 60 days of treatment of the initial episode (Bouza et al., 2006, supra; McFarland 2009, supra). After first recurrence, 40% will have another recurrence, and after two recurrences the likelihood of having additional episodes of CDI increases further (Bouza et al., 2006, supra; McFarland 2009, supra).

Bezlotoxumab is a human monoclonal antibody (mAb) that binds to and neutralizes *C. difficile* toxin B (TcdB), and was recently approved by the FDA to reduce recurrence of *Clostridium difficile* infection (CDI) in patients 18 years of age or older who are receiving antibacterial drug treatment of CDI and are at a high risk for CDI recurrence. Phase 3 clinical trials have demonstrated that in patients with CDI and receiving antibiotic therapy, intravenous (IV) administration of a single 10 mg/kg dose of bezlotoxumab is safe and efficacious in preventing CDI recurrence. Despite the beneficial impact expected by the availability of a new treatment for the prevention of CDI recurrence, the therapeutic effect of a medicament that targets *C. difficile* toxin B can vary widely among patients afflicted with *Clostridium difficile* infection. In order to provide better and more cost-effective treatments for CDI, a need exists for a method to identify patients who are most likely to benefit through treatments with a medicament that targets *C. difficile* toxin B, e.g. a TcdB antibody.

SUMMARY OF THE INVENTION

The present invention is based on the discovery that genetic variation on human chromosome 6, such as single nucleotide polymorphisms (SNPs), and different human leukocyte antigen (HLA) alleles, are significantly associated with response to treatment with a *C. difficile* toxin B ("TcdB") antibody in patients suffering from a *Clostridium difficile* infection (CDI) and/or *Clostridium difficile* associated disease (CDAD) and or the symptoms thereof. The genetic polymorphisms and variant alleles associated with response to treatment with a medicament that targets TcdB are referred to herein as the "TcdB treatment response markers."

In one embodiment of the invention, the TcdB treatment response marker is an SNP which is a C/T polymorphism, identified as rs2516513 in the NCBI SNP database. The presence of the T allele is associated with a better treatment response, whether present in the homozygous (T/T) or heterozygous (C/T) state. Collectively, the T/T and C/T genotypes are associated with a ~2-fold reduction in *C. difficile* recurrence rate compared to overall unstratified patient population treated with bezlotoxumab for CDI. While the T allele has a less frequent prevalence than the C allele in most ethnic populations (minor allele), it is common in many ethnic populations, and may guide medical practitioners, health authorities, and medical insurance providers in selecting a suitable population of *C. difficile* infected patients which might benefit from a TcdB medicament, e.g. a TcdB antibody.

The inventors also identified associations between other genetic variations on chromosome 6 with a beneficial response to treatment with a medicament that targets TcdB, e.g., improvements in *C. difficile* recurrence rates in patients with CDI. The genetic variants associated with a beneficial response treatment to a treatment that targets TcdB, e.g. a TcdB antibody, are described in Table 1 below, wherein PS means polymorphic site according to the SNP NCBI database.

TABLE 1

TcdB Treatment Response Markers

| Polymorphic Site (PS) | Alleles | Better Response Allele |
| --- | --- | --- |
| rs2516513 | C/T | T |
| HLA-DRB1 | HLA-DRB1*X[a] | HLA-DRB1*07:01 |
| rs113379306 | A/C | A |
| rs76166871 | A/G | A |
| HLA-DQB1 | HLA-DQB1*X[b] | HLA-DQB1*02:02 |
| HLA-DQA1 | HLA-DQA1*X[c] | HLA-DQA1*02:01 |

*X[a] represents all HLA-DRB1 alleles other than HLA-DRB1*07:01;
X[b] represents all HLA-DQB1 alleles other than HLA-DQB1*2:02;
X[c] represents all HLA-DQA1 alleles other than HLA-DQA1*02:01.

The inventors herein contemplate that testing individuals for the presence of one or more of the TcdB treatment response markers in Table 1 will be useful in a variety of pharmacogenetic products and methods that involve identifying patients most likely to respond to therapy with a medicament that targets TcdB in patients with CDI, and in helping health care providers decide whether to prescribe such a medicament, e.g. a TcdB antibody, to a patient with CDI or a patient who has had CDI. For instance, the inventors contemplate that testing subjects for the presence of at least one copy (i.e. heterozygosity or homozygosity) of one or more of the TcdB treatment response markers described on Table 1; namely the T allele for the rs2516513 SNP, the A allele for rs113379306, the A allele for the rs76166871 SNP, the HLA-DRB1*07:01 allele, the HLA-DQB1*02:02 allele, or the HLA-DQA1*02:01 allele will be useful for such products and methods, and in helping such health care providers.

All of the SNPs and alleles in Table 1 (HLA-DRB1*07:01, rs2516513, rs113379306, rs76166871, HLA-DQB1*02:02 and HLA-DQA1*02:01) are useful either alone or in combination for predicting CDI recurrence. In addition, SNPs and genetic variants in linkage disequilibrium (LD) with the SNPS in Table 1 can be used alone or in combinations with the SNPs and alleles in Table 1.

Additionally, as described above for the rs2516513 SNP, the overall frequency in the population of the TcdB treatment response markers of the invention may have a less frequent prevalence in the population at large than in specific subgroups or ethnic populations. See, e.g. Table 1A below, which provides the frequencies of the HLA-DRB1*07:01 allele, the HLA-DQB1*02:02 allele, and the HLA-DQA1*02:01 allele in example ethnic populations. The frequencies provided are for various specific subgroups and represent a sampling of representative populations. Frequencies in other populations not listed will vary, and can be obtained from Gonzalez-Galarza et al., Allele Frequency Net 2015 Update: New Features for HLA Epitopes, KIR and Disease and HLA Adverse Drug Reaction Associations. Nucleic Acid Research 2015, 28, D784-8. Such information may be useful in selecting a suitable population of *C. difficile* infected patients which might benefit from a TcdB medicament, e.g. a TcdB antibody.

TABLE 1A

Frequency of HLA Alleles in Specific Studied Populations

| | Percent of Individuals That Have the Specified Allele/Allele Frequency | | | | | |
| --- | --- | --- | --- | --- | --- | --- |
| Population | HLA-DRB1*07:01 | | HLA-DQB1*02:02 | | HLA-DQA1*02:01 | |
| Argentina Buenos Aires | 25.1/ | 0.135 | | | 25.7 | 0.139 |
| Czech Republic pop 2 | 36.4 | 0.202 | | | 36.4 | 0.202 |
| France West | 18 | 0.094 | 17 | 0.089 | | |
| Greece | 6 | 0.031 | | | 2 | 0.01 |
| India Lucknow | 38 | 0.198 | | | 39.2 | 0.203 |
| Ireland South | 29.6 | 0.162 | 17.6 | 0.098 | | |
| Ireland North | 0 | 0 | | | | |
| Japan South | 0.8 | 0.004 | | | | |
| Portugal Azores Terceira Island | 31.6 | 0.175 | 31.6 | 0.167 | 29.8 | 0.167 |
| Saudi Arabia pop 5 | 44.3 | 0.266 | 24.7 | 0.142 | | |
| Spain Barcelona | 30 | 0.163 | | | | |
| USA Philadelphia Caucasian | 29.8 | 0.174 | 25.5 | 0.152 | | |
| USA Southern California Mestizo | 17.8 | 0.093 | 9.6 | 0.049 | | |

By "testing subjects for the presence of at least one copy of one or more of the TcdB treatment response markers" herein, it is meant that for use in the methods of the invention, subjects can be tested for one, two, three, four, five or six of the Tcd treatment response markers of the invention, in any combination, as well as in combinations with linked variants of the TcdB treatment response markers of the invention, as described, infra.

Thus, the invention relates to a method of preventing the recurrence of a *Clostridium difficile* (*C. difficile*) infection comprising: administering a therapeutically effective amount of a treatment that targets *C. difficile* toxin B (TcdB treatment) to a patient in need thereof, wherein said patient, prior to the administration of the TcdB treatment, has tested positive for at least one copy of a better response allele from one or more TcdB treatment response markers, or linked variants (i.e., variants in high LD) of the TcdB treatment response markers; wherein the one or more TcdB treatment response marker is selected from the group consisting of: (a) the T allele of the rs2516513 single nucleotide polymorphism (SNP); (b) the A allele of the rs113379306 SNP; (c) the A allele of the rs76166871 SNP; (d) the HLA-DRB1*07:01 allele of the HLA-DRB1 gene; (e) the HLA-DQB1*02:02 allele of the HLA-DQB1 gene; and (f) the HLA-DQA1*02:01 allele of the HLA-DQA1 gene.

Also provided herein is a method of determining if a patient is likely to respond to a medicament that targets *C. difficile* toxin B (TcdB) in a human patient, said method comprising: (a) obtaining or having obtained a biological sample from said patient; (b) determining whether a better response allele of at least one TcdB response marker of the invention, or a linked variant, is present in the biological sample; and (c) diagnosing the patient as more likely to benefit to treatment with a TcdB medicament when the presence of one or more copies of the better response allele in the biological sample is detected.

In some embodiments of this aspect of the invention, the method further comprises step (d), which comprises administering a therapeutically effective amount of the TcdB medicament to the diagnosed patient.

In preferred embodiments of the methods provided herein, the treatment that targets TcdB is a TcdB antibody or an antigen binding fragment thereof. In further preferred embodiments, the TcdB antibody is bezlotoxumab.

The invention further relates to a drug product which comprises a pharmaceutical composition and prescribing information, wherein the pharmaceutical composition comprises a TcdB antibody and the prescribing information comprises a pharmacogenetic indication, wherein the pharmacogenetic indication comprises treatment of *C. difficile* infection or the prevention of *C. difficile* recurrence in patients infected with *C. difficile* who test positive for at least one copy of a better response allele selected from a TcdB treatment response marker of the invention, or a linked variant.

Also provided by the invention are kits for testing a patient for the presence or absence of at least one copy of a better response allele selected of a TcdB treatment response marker of the invention, wherein the kit comprises a set of reagents which may include oligonucleotides designed to genotype at least one of the TcdB treatment response markers.

The invention also includes the use of bezlotoxumab in the manufacture of a medicament for the prevention of *C. difficile* recurrence in a human patient, wherein the patient has tested positive for a better response allele of a TcdB treatment response marker disclosed herein.

BRIEF DESCRIPTION OF THE DRAWINGS

FIG. 2 provides an analysis of the proportion of subjects with CDI recurrence (PN001+PN002, full analysis set ("FAS") population) following treatment with actoxumab/bezlotoxumab (MK3415A), bezlotoxumab (MK-6072), or placebo.

FIG. 3 provides a summary of CDI recurrence by high-risk subgroup (PN001+PN002, FAS population).

FIG. 4 shows the percentage and numbers of subjects with CDI recurrence in the different treatment arms of PN001 and PN002 and the subjects used in the genome wide association study ("GWAS") analyses.

FIG. 5A provides examples of SNPs in linkage disequilibrium (LD) with rs2516513, FIG. 5B provides examples of SNPs in LD with rs113379306, and FIG. 5C provides examples of SNPs in LD with rs76166871.

FIG. 10 shows a significant reduction in the rate of rCDI occurred in BEZ-treated participants who carried the T allele of rs2516513 (−21.5% risk difference with p-value=3.04E-05 versus −10.7% risk difference overall without genotype stratification) and the HLA-DRB1*07:01 allele (−32.3% risk difference with p-value=1.95E-05 versus −10.5% risk difference overall without genotype stratification) compared with PBO recipients.

FIG. 11 shows that the reduction in risk of rCDI in BEZ-treated participants carrying the T allele of rs2516513 and HLA-DRB1*07:01 compared with PBO recipients varied according to risk factors.

DETAILED DESCRIPTION OF THE INVENTION

Definitions and Abbreviations

Figure 1:
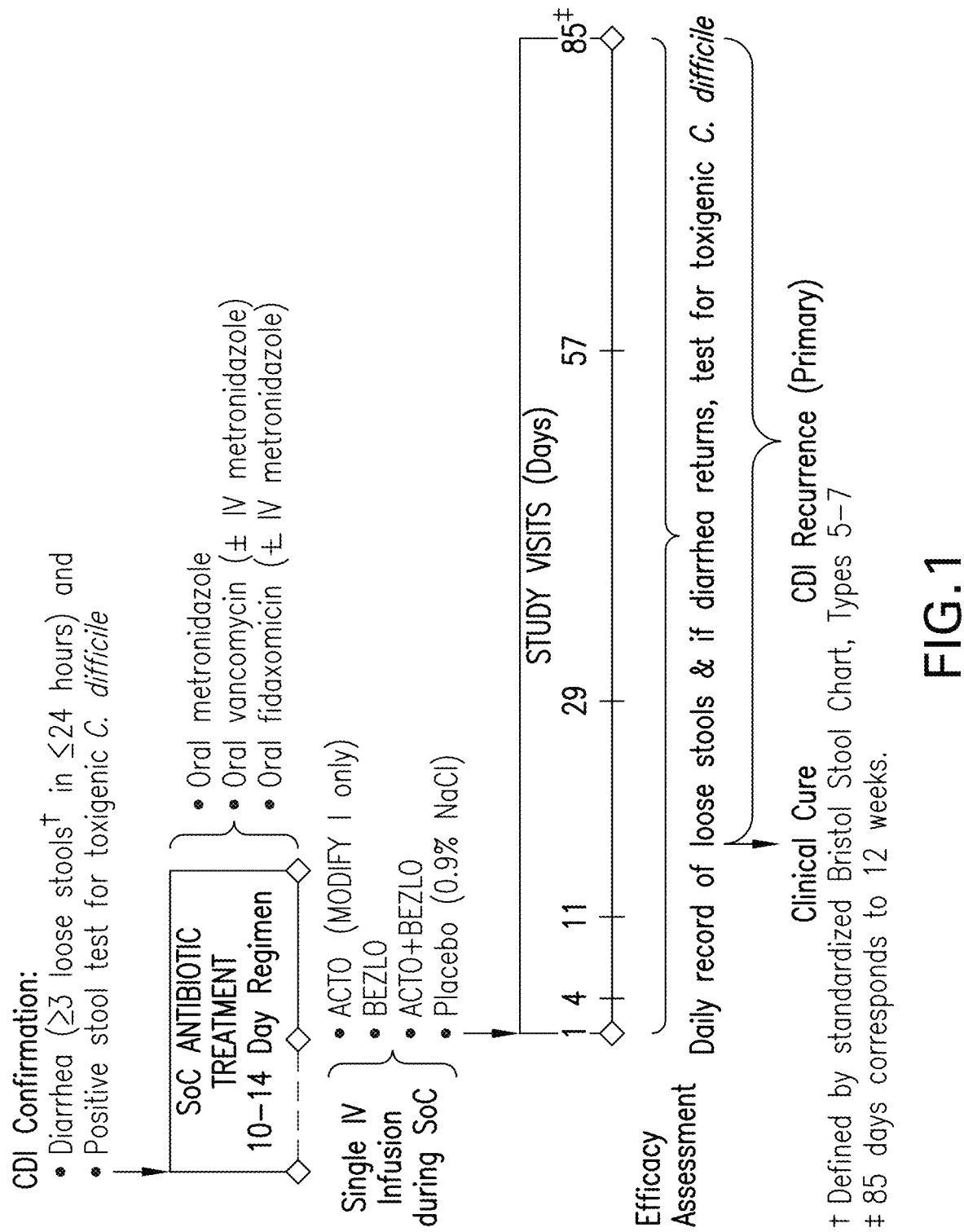
FIG. 1 is graphical depiction of the study design "MODIFY I" ("PN001", ClinicalTrials.gov Identifier: NCT01241552) and "MODIFY II" ("PN002", ClinicalTrials.gov Identifier: NCT01513239) used in measuring the efficacy of patients treated with a TcdB antibody, i.e. bezlotoxumab.

So that the invention may be more readily understood, certain technical and scientific terms are specifically defined below. Unless specifically defined elsewhere in this document, all other technical and scientific terms used herein have the meaning that would be commonly understood by one of ordinary skill in the art to which this invention belongs when used in similar contexts as used herein.

As used herein, including the appended claims, the singular forms of words such as "a," "an," and "the," include their corresponding plural references unless the context clearly dictates otherwise.

"About" when used to modify a numerically defined parameter, e.g., the dosage for a therapeutic agent discussed herein, or the length of treatment time, means that the parameter may vary by as much as 10% above or below the stated numerical value for that parameter.

"Actoxumab" (alternatively referred to herein as "ACT", also known as MK3415) is a fully human IgG1 monoclonal antibody (mAb) that specifically binds to the receptor binding domain of *C. difficile* toxin A. Actoxumab comprises light chain CDRs (CDRL1, CDRL2, and CDRL3) consisting of a sequence of amino acids as set forth in SEQ ID NOs: 10, 11, and 12, respectively, and heavy chain CDRs (CDRH1, CDRH2, and CDRH3) consisting of a sequence of amino acids as set forth in SEQ ID NOs: 14, 15, and 16, respectively. Actoxumab comprises a $V_L$ region comprising a sequence of amino acids as set forth in SEQ ID NO:9 and a $V_H$ region comprising a sequence of amino acids as set forth in SEQ ID NO:13.

"Actoxumab/bezlotoxumab" (alternatively referred to herein as "ACT+BEZ", also known as MK3415A) refers to the combination of the actoxumab and bezlotoxumab antibodies and/or the use of such combination for treating patients with CDI, including prevention of recurrence of CDI.

"Allele" is a particular form of a gene or other genetic locus, distinguished from other forms by its particular permutation of nucleotide sequences, the term allele also includes any of the alternative forms of the gene at that genetic locus.

"Beneficial result" means a desired clinical result of treatment with a medicament that targets TcdB, e.g. TcdB antibody, including but not limited to: alleviation of one or more disease symptoms, diminishment of extent of disease (e.g., improvement in *C. difficile* recurrence rate in the context of the treatment of CDI), stabilized (i.e., not worsening) state of disease, slowing of disease progression, amelioration or palliation of a disease state, prolonging survival (as compared to expected survival if not treated), relapse-free survival, remission (whether partial or total) and cure (i.e., elimination of the disease).

"Better response allele" is the particular form of a gene or other genetic locus, where if present in a patient, results in an improved clinical measure (e.g., an improved *C. difficile* recurrence rate measure) as compared to the measure in a patient where such form of the gene or other genetic locus is absent.

"Bezlotoxumab" (alternatively referred to herein as "BEZ", also known as MK-6072) is a fully human mAb of the IgG1/kappa isotype subclass that binds with high affinity to the C-terminus ligand binding region of *C. difficile* toxin B (Kd=19 pM) (U.S. Pat. No. 8,394,819, the disclosure of which is hereby incorporated by reference in its entirety). Bezlotoxumab is currently being developed for the prevention of CDI recurrence in patients 18 years or older receiving antibiotic therapy for CDI. Bezlotoxumab comprises light chain CDRs (CDRL1, CDRL2, and CDRL3) consisting of a sequence of amino acids as set forth in SEQ ID NOs: 2, 3, and 4, respectively, and heavy chain CDRs (CDRH1, CDRH2, and CDRH3) consisting of a sequence of amino acids as set forth in SEQ ID NOs: 6, 7, and 8, respectively. Bezlotoxumab comprises a $V_L$ region comprising a sequence of amino acids as set forth in SEQ ID NO:1 and a $V_H$ region comprising a sequence of amino acids as set forth in SEQ ID NO:5.

"CDI recurrence" refers generally to a new episode of CDI in a patient, following a prior episode in the patient that had been resolved. More specifically, CDI recurrence in a patient is diagnosed by the development of new symptoms of CDAD, e.g. the development of a new episode of diarrhea, with a positive *C. difficile* stool toxin(s) test after the resolution of the prior episode and after discontinuation of standard of care therapy.

"Consists essentially of" and variations such as "consist essentially of" or "consisting essentially of" as used throughout the specification and claims, indicate the inclusion of any recited elements or group of elements, and the optional inclusion of other elements, of similar or different nature than the recited elements, which do not materially change the basic or novel properties of the specified dosage regimen, method, or composition.

A "patient" (alternatively referred to herein as a "subject" or an "individual") refers to a mammal capable of being infected with *C. difficile*. In preferred embodiments, the patient is a human. In additional preferred embodiments, the individual is an adult human, i.e., at least 18 years of age. A patient can be treated prophylactically or therapeutically. Prophylactic treatment provides sufficient active pharmaceutical ingredient (e.g., TcdB antibody) to reduce the likelihood or severity of a *C. difficile* infection or recurrence or the effects thereof, i.e., CDAD. Therapeutic treatment (e.g. antibiotic) can be performed to ameliorate or abrogate a *C. difficile* infection or the effects thereof, or to reduce the severity of *C. difficile* infection or of CDAD.

A "high risk" patient is a patient with 1 or more of the following risk factors for recurrent CDI: prior episode of CDI in the past 6 months, severe CDI at baseline (per Zar score, as described in Zar et al., A comparison of vancomycin and metronidazole for the treatment of *Clostridium difficile*-associated diarrhea, stratified by disease severity. *Clin. Infect. Dis.* 45: 302-307 (2007)), age.≥65 years, CDI due to a hypervirulent strain (027, 078, or 244 ribotypes), immunocompromised, received concomitant systemic antibiotics.

Those "in need of treatment" include those already with a *C. difficile* infection, as well as those prone to have an infection or any person in which a reduction in the likelihood of infection is desired, or individuals who are displaying symptoms of CDAD. Individuals prone to CDI include those who have recently suffered from a *C. difficile* infection, whether or not such individual tests positive for CDI at the time the particular treatment is given. For example, a patient in need of treatment with a medicament that targets TcdB may include a patient who is currently suffering from a CDI, or a person who has recently had a CDI that is undetectable at the time of treatment, e.g. a person who tested positive for CDI 1 month prior to treatment with the TcdB medicament, or 3 weeks, 2 weeks, 1 week, 6 days, 5 days, 4 days, 3 days, 2 days or 1 day prior to treatment with the TcdB medicament. Persons with an increased risk of *C. difficile* infection include those undergoing antibiotic treatment, e.g. treatment with certain clindamycin, cephalosporins, and fluoroquinolones, as well as patients of advanced age (>65 years), patients that are immunosuppressed, patients who are health care workers, and patients undergoing an extended duration of hospitalization.

"Isolated" is typically used to reflect the purification status of a biological molecule such as RNA, DNA, oligonucleotide, or protein, and in such context means the molecule is substantially free of other biological molecules such as nucleic acids, proteins, lipids, carbohydrates, or other material such as cellular debris and growth media. Generally, the term "isolated" is not intended to refer to a complete absence of other biological molecules or material or to an absence of water, buffers, or salts, unless they are present in amounts that substantially interfere with the methods of the present invention.

"Locus" refers to a location on a chromosome or DNA molecule corresponding to a gene, a physical feature such as a polymorphic site, or a location associated with a phenotypic feature.

"Nucleotide pair" is the set of two nucleotides (which may be the same or different) found at a polymorphic site on the two copies of a chromosome from an individual.

"Oligonucleotide" refers to a nucleic acid that is usually between 5 and 100 contiguous bases in length, and most frequently between 10-50, 10-40, 10-30, 10-25, 10-20, 15-50, 15-40, 15-30, 15-25, 15-20, 20-50, 20-40, 20-30 or 20-25 contiguous bases in length. The sequence of an oligonucleotide can be designed to specifically hybridize to any of the allelic forms of a locus; such oligonucleotides are referred to as allele-specific probes. If the locus is a PS comprising a SNP, the complementary allele for that SNP can occur at any position within an allele-specific probe. Other oligonucleotides useful in practicing the invention specifically hybridize to a target region adjacent to a PS with their 3' terminus located one to less than or equal to about 10 nucleotides from the PS, preferably about 5 nucleotides. Such oligonucleotides hybridizing adjacent to a PS are useful in polymerase-mediated primer extension methods and are referred to herein as "primer-extension oligonucleotides". In a preferred embodiment, the 3'-terminus of a primer-extension oligonucleotide is a deoxynucleotide complementary to the nucleotide located immediately adjacent to the PS.

"Pharmaceutically acceptable" refers to molecular entities and compositions that are "generally regarded as safe," e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

"Polymorphic site" or "PS" refers to the position in a genetic locus or gene at which a polymorphism is found, e.g., single nucleotide polymorphism (SNP), restriction fragment length polymorphism (RFLP), variable number of tandem repeat (VNTR), dinucleotide repeat, trinucleotide repeat, tetranucleotide repeat, simple sequence repeat, insertion element such as Alu, and deletion or insertion of one or more nucleotides. A PS is usually preceded by and followed by highly conserved sequences in the population of interest and thus the location of a PS is typically made in reference to a consensus nucleic acid sequence of thirty to sixty nucleotides that bracket the PS, which in the case of a SNP is commonly referred to as the "SNP context sequence". The location of the PS may also be identified by its location in a consensus or reference sequence. The skilled artisan understands that the location of a particular PS may not occur at precisely the same position in a reference or context sequence in each individual in a population of interest due to the presence of one or more insertions or deletions in that individual as compared to the consensus or reference sequence. Moreover, it is routine for the skilled artisan to design robust, specific and accurate assays for detecting the alternative alleles at a polymorphic site in any given individual, when the skilled artisan is provided with the identity of the alternative alleles at the PS to be detected and one or both of a reference sequence or context sequence in which the PS occurs. Thus, the skilled artisan will understand that specifying the location of any PS described herein by reference to a particular position in a reference or context sequence is merely for convenience and that any specifically enumerated nucleotide position literally includes whatever nucleotide position the same PS is actually located at in the same locus in any individual being tested for the presence or absence of a genetic marker of the invention using any of the genotyping methods described herein or other genotyping methods well-known in the art.

"Reference SNP" or "rs" number refers to an accession number assigned to an individual SNP by the National Center for Biotechnology Information (NCBI).

"TcdA" refers to toxin A of *C. difficile*, which is a large clostridial toxin from toxigenic isolates of *Clostridium difficile*.

"TcdB" refers to toxin B of *C. difficile*, which is a large clostridial toxin from toxigenic isolates of *Clostridium difficile*.

"TcdA antibody" refers to an antibody that specifically binds to toxin A of *Clostridium difficile*, e.g., actoxumab.

"TcdB antibody" refers to an antibody that specifically binds to toxin B of *Clostridium difficile*, e.g., bezlotoxumab.

"TcdB medicament" refers to a pharmaceutical or biological therapeutic agent that targets *C. difficile* toxin B. As defined herein, a TcdB medicament includes both small molecule and biologic drugs, such as antibodies, or antigen binding fragments thereof.

"TcdB treatment response marker(s)" alternatively "TcdB medicament response marker" refers to a genetic marker of the invention, which is useful for predicting response of a patient to a TcdB medicament.

"Treat" or "Treating" means to administer a therapeutic agent, such as a composition containing an TcdB antibody described herein, internally or externally to an individual in need of the therapeutic agent. Typically, the therapeutic agent is administered in a therapeutically effective amount, which means an amount effective to produce one or more beneficial results. The therapeutically effective amount of a particular agent may vary according to factors such as the disease state, age, and weight of the patient being treated, and the sensitivity of the patient, e.g., ability to respond, to the therapeutic agent. Whether a beneficial or clinical result has been achieved can be assessed by any clinical measurement typically used by physicians, physician's assistants or other skilled healthcare providers to assess the presence, severity or progression status of the targeted disease, symptom or adverse effect. Typically, a therapeutically effective amount of an agent will result in an improvement in the relevant clinical measurement(s) over the baseline status, or over the expected status if not treated, of at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%. For instance, in one embodiment wherein the condition or disorder is *C. difficile* infection, a clinical measure of improvement is an improvement in the *C. difficile* recurrence rate measure. While an embodiment of the present invention (e.g., a treatment method or article of manufacture) may not achieve the desired clinical benefit or result in every patient, it should do so in a statistically significant number of patients as determined by any statistical test known in the art such as the likelihood ratio test based logistic regression with 2 degree freedom, etc.

The following abbreviations are used throughout the text and have the following meanings:
ASO allele-specific oligonucleotide
CDAD *Clostridium difficile*-associated disease
CDI *Clostridium difficile* infection
CDR complementarity determining region
GWAS genome wide association study
HLA human leukocyte antigen
LD linkage disequilibrium
mAB monoclonal antibody
PCR polymerase chain reaction
PS polymorphic site
rCDI recurrent CDI
RFLP restriction fragment length polymorphism
SNP single nucleotide polymorphism
TcdA *Clostridium difficile* toxin A
TcdB *Clostridium difficile* toxin B
$V_H$ variable heavy region of an antibody
$V_L$ variable light region of an antibody
VNTR variable number of tandem repeat Utility of the TcdB Treatment Response Markers of the Invention The phenotypic effect of the response markers described herein supports the use of these markers in a variety of commercial applications, including but not limited to, clinical trials of investigational or previously approved TcdB medicaments in patients selected on the basis of the presence or absence of a genetic response marker of the invention, pharmaceutical compositions and drug products comprising a TcdB therapeutic agent (e.g. small molecule, antibody, or antigen binding fragment thereof) for treating patients who have a TcdB treatment response marker of the invention, in diagnostic methods, and in pharmacogenetic treatment methods, which involve tailoring a patient's drug therapy based on whether the patient has at least one TcdB treatment response marker of the invention.

The utility of any of the commercial applications claimed herein does not require that the correlation between the presence of a response marker of the invention and the occurrence of the desired response to the TcdB medicament or TcdB antibody be observed in 100% of the individuals that receive the TcdB medicament or TcdB antibody; nor does it require a diagnostic method or kit to have a specific degree of specificity or sensitivity in determining the presence or absence of the response marker in every individual, nor does it require that a diagnostic method claimed herein be 100% accurate in predicting for every individual whether the individual is likely to have a beneficial response to a TcdB medicament or TcdB antibody. Thus, the inventors herein intend that the terms "determine", "determining" and "predicting" should not be interpreted as requiring a definite or certain result; instead these terms should be construed as meaning that a claimed method provides an accurate result for the majority of individuals, or that the result or prediction for any given individual is more likely to be correct than incorrect.

Preferably, the accuracy of the result provided by a diagnostic method of the invention is one that a skilled artisan or regulatory authority would consider suitable for the particular application in which the method is used. Similarly, the utility of the claimed drug products and treatment methods does not require that they produce the claimed or desired effect in every individual; all that is required is that a clinical practitioner, when applying his or her professional judgment consistent with all applicable norms, decides that the chance of achieving the claimed effect of treating a given individual according to the claimed method or with the claimed drug product is sufficiently high to warrant prescribing the treatment or drug product.

Testing for a TcdB Treatment Response Marker of the Invention

The presence or absence of the TcdB treatment response markers of the invention may be detected by any of a variety of genotyping or sequencing techniques commonly used in the art. Technologies that may be used in genotyping an individual at the genomic positions of the TcdB treatment response markers of the invention include, but are not limited to: sequencing and next generation sequencing technologies, RNA sequencing, mass spectrometry, comparative genomic hybridization, SNP-based arrays, restriction fragment length polymorphism, Sanger sequencing, chemical sequencing (e.g. Maxam and Gilbert), denaturing high-performance liquid chromatography, DNA hybridization techniques, and PCR. One of skill in the art will be able to select any of the many techniques available to determine the genotype of an individual of one or more TcdB treatment response markers. These techniques allow not only the detection of the presence or absence of a specific TcdB treatment response marker of the invention, but also the determination of if the individual is heterozygous or homozygous at that site.

Exemplary genotyping or sequencing techniques may employ one or more oligonucleotides that are complementary to a region containing, or adjacent to, the PS of interest however hybridization methods and alternative methods for detecting variants or polymorphic sites may be used. The sequence of an oligonucleotide used for genotyping a particular PS of interest is typically designed based on a context sequence for the PS.

The location, in a particular individual, of the polymorphic site identified above is in a reference coding or genomic DNA sequence surrounding the PS of interest or in one of the context sequences described in Table 2 below, or their complementary sequences. Table 2 shows the context nucleic acid sequences for the SNPs determined to be TcdB treatment response markers in accordance with the invention. It was also shown herein that the three HLA alleles: HLA-DRB1*07:01, HLA-DQB1*02:02, and HLA-DQA1*02:01 are TcdB treatment response markers in accordance with the invention.

TABLE 2

Context sequences for SNPs associated with TcdB Treatment Response

| PS | Short Context Sequences[1] | SEQ ID NO: | Location[3] |
|---|---|---|---|
| rs2516513 | TTCAAATCTCTGCTCY$^a$TCATTTCACACCATCT AGATGGTGTGAAATGAY$^b$GAGCAGAGATTTGA AA[2] | 17 18 | 6: 31479811 |
| rs113379306 | TGTCTTTCAAAACTCTGATTTGAGGY$^c$ATGTTG GACCTCCCTTTCTATCTTC GAAGATAGAAAGGGAGGTCCAACATY$^d$CCTCA AATCAGAGTTTTGAAAGACA | 19 20 | 6: 17333120 |
| rs76166871 | CGGGAGGTCGAGGCTGCAGTGAGCCY$^e$TCATT GCACCATTGCACTCCAGCCT AGGCTGGAGTGCAATGGTGCAATGAY$^f$GGCTC ACTGCAGCCTCGACCTCCCG | 21 22 | 6: 17329709 |

[1]Unless otherwise indicated, context sequences provided are as reported in the NCBI dbSNP Database on Jun. 23, 2016;
[2]context sequence is reverse complement of context sequence reported in NCBI;
[3]location on human chromosome 6, as reported in NCBI dbSNP database on Oct. 31, 2016;
Y$^a$ indicates T or C; Y$^b$ indicates A or G; Y$^c$ indicates A or C; Y$^d$ indicates T or G; Y$^e$ indicates A or G; Y$^f$ indicates T or C.

As recognized by the skilled artisan, nucleic acid samples containing a particular PS may be complementary double stranded molecules and thus reference to a particular site on the sense strand refers as well to the corresponding site on the complementary antisense strand. Similarly, reference to a particular genotype obtained for a PS on both copies of one strand of a chromosome is equivalent to the complementary genotype obtained for the same PS on both copies of the other strand. By way of example, a C/C genotype for the rs2516513 PS on the sense strand for the gene is equivalent to a G/G genotype for that PS on the antisense strand.

The context sequences recited herein, as well as their complementary sequence, may be used to design probes and primers for genotyping the TcdB treatment response markers in a nucleic acid sample obtained from a human subject of interest using any of a variety of methods well known in the art that permits the determination of whether the individual has at least one copy of a better response allele of one or more TcdB treatment response markers identified herein. Nucleic acid molecules utilized in such methods generally include RNA, genomic DNA, or cDNA derived from RNA.

Typically, genotyping methods involve assaying a nucleic acid sample prepared from a biological sample obtained from the individual to determine the identity of a nucleotide or nucleotide pair present at one or more polymorphic sites of interest. Nucleic acid samples may be prepared from virtually any biological sample. For example, convenient samples include whole blood serum, semen, saliva, tears, fecal matter, urine, sweat, buccal matter, skin and hair. Non-malignant somatic cells are preferred since they allow the determination of the identity of both alleles present at the PS of interest, without contamination by tumor-specific mutations.

Nucleic acid samples may be prepared for analysis using any technique known to those skilled in the art. Preferably, such techniques result in the isolation of genomic DNA sufficiently pure for determining the genotype for the desired polymorphic site(s) in the nucleic acid molecule. To enhance the sensitivity and specificity of that determination, it is frequently desirable to amplify from the nucleic acid sample a target region containing the PS to be genotyped. Nucleic acid isolation and amplification techniques may be found, for example, in Sambrook, et al., Molecular Cloning: A Laboratory Manual (Cold Spring Harbor Laboratory, New York) (2001).

Any amplification technique known to those of skill in the art may be used in practicing the present invention including, but not limited to, polymerase chain reaction (PCR) techniques. PCR may be carried out using materials and methods known to those of skill in the art (See generally PCR Technology: Principals and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Matilla et al., *Nucleic Acids Res.* 19: 4967 (1991); Eckert et al., PCR Methods and Applications 1: 17 (1991); PCR (eds. McPherson et al., IRL Press, Oxford); and U.S. Pat. No. 4,683,202. Other suitable amplification methods include the ligase chain reaction (LCR) (see Wu and Wallace, Genomics 4: 560 (1989) and Landegren et al., *Science* 241: 1077 (1988)), transcription amplification (Kwoh et al., *Proc. Natl. Acad. Sci. USA* 86: 1173 (1989)), self-sustained sequence replication (Guatelli et al., *Proc. Nat. Acad. Sci. USA,* 87: 1874 (1990)); isothermal methods (Walker et al., *Proc. Natl. Acad. Sci. USA* 89:392-6 (1992)); and nucleic acid-based sequence amplification (NASBA).

The amplified target region is assayed to determine the identity of at least one of the alleles present at a PS in the target region. If both alleles of a locus are represented in the amplified target, it will be readily appreciated by the skilled artisan that only one allele will be detected at a PS in individuals who are homozygous at that PS, while two different alleles will be detected if the individual is heterozygous for that PS.

The identity of the allele may be identified directly, known as positive-type identification, or by inference, referred to as negative-type identification. For example, where a SNP is known to be guanine or cytosine in a reference population, a PS may be positively determined to be either guanine or cytosine for an individual homozygous at that site, or both guanine and cytosine, if the individual is heterozygous at that site. Alternatively, the PS may be negatively determined to be not guanine (and thus cytosine/cytosine) or not cytosine (and thus guanine/guanine). In either case, where it is determined that at least one copy of a better response allele is present as set forth in Table 1, that determination is deemed to be a positive test result for the better response allele in the methods, uses, drug products, or kits described herein.

Identifying the allele or pair of alleles (e.g., the two nucleotides in case of a SNP) at a PS in a nucleic acid sample obtained from an individual may be accomplished using any technique known to those of skill in the art. Preferred techniques permit rapid, accurate assaying of multiple PS with a minimum of sample handling. Some examples of suitable techniques include, but are not limited to, direct DNA sequencing of the target region (with or without amplification), capillary electrophoresis, hybridization of allele-specific probes, single-strand conformation polymorphism analysis, denaturing gradient gel electrophoresis, temperature gradient electrophoresis, mismatch detection; nucleic acid arrays, primer specific extension, protein detection, imputation and other techniques well known in the art. See, for example, Sambrook, et al., Molecular Cloning: A Laboratory Manual (Cold Spring Harbor Laboratory, New York) (2001); Ausubel, et al., Current Protocols in Molecular Biology (John Wiley and Sons, New York) (1997); Orita et al., *Proc. Nat. Acad. Sci. USA* 86, 2766-2770 (1989); Humphries et al., in Molecular Diagnosis of Genetic Diseases, ed., pp. 32 1-340, 1996; Wartell et al., *Nucl. Acids Res.* 18:2699-706 (1990); Hsu et al. (1994) *Carcinogenesis* 15:1657-1662; Sheffield et al., *Proc. Natl. Acad. Sci. USA* 86:232-6 (1989); Winter et al., *Proc. Natl. Acad. Sci. USA* 82:7575 (1985); Myers et al. (1985) *Nature* 313:495; Rosenbaum and Reissner (1987) *Biophys Chem.* 265:12753; Modrich, *Ann. Rev. Genet.* 25:229-53 (1991); Howie et al., Fast and accurate genotype imputation in genome-wide association studies through pre-phasing. *Nature Genetics* 44(8): 955-959 (2012); U.S. Pat. Nos. 6,300,063; 5,837,832; 5,459,039; and HuSNP Mapping Assay, reagent kit and user manual, Affymetrix Part No. 90094 (Affymetrix, Santa Clara, CA).

In some embodiments, the identity of the allele(s) at a PS is determined using a polymerase-mediated primer extension method. Several such methods have been described in the patent and scientific literature and include the "Genetic Bit Analysis" method (WO 92/15712) and the ligase/polymerase mediated genetic bit analysis (U.S. Pat. No. 5,679,524). Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798.

Another primer extension method employs allele specific PCR (Ruano, G. et al., *Nucl. Acids Res.* 17:8392 (1989); Ruano, G. et al., *Nucl. Acids Res.* 19:6877-82 (1991); WO 93/22456; Turki et al., *J. Gun. Invest.* 95:1635-41 (1995)).

Yet another primer extension method for identifying and analyzing polymorphisms utilizes single-base extension (SBE) of a fluorescently-labeled primer coupled with fluorescence resonance energy transfer (FRET) between the label of the added base and the label of the primer. Typically, the method, such as that described by Chen et al., *Proc. Nat. Acad. Sci.* 94:10756-61 (1997) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

One example of a genotyping assay is a TaqMan® SNP Genotyping Assay from Thermo Fisher Scientific, Waltham, Massachusetts, USA, or an assay having about the same reliability, accuracy and specificity. In certain embodiments of such an assay, two allele-specific probes are used to target a specific PS, with each probe having a distinct fluorescent label bonded to it as well as a quencher molecule. In addition, two allele-specific primers are used. Upon extension of the DNA strand, the Taq DNA polymerase cleaves the fluorescent label which cleavage results in fluorescence emissions which can be detected.

In all of the above methods, the accuracy and specificity of an assay designed to detect the identity of the allele(s) at any PS is typically validated by performing the assay on DNA samples in which the identity of the allele(s) at that PS is known. Preferably, a sample representing each possible allele is included in the validation process. For diploid loci such as those on autosomal chromosomes, the validation samples will typically include a sample that is homozygous for the major allele at the PS, a sample that is homozygous for the minor allele at the PS, and a sample that is heterozygous at that PS. These validation samples are typically also included as controls when performing the assay on a test sample (i.e., a sample in which the identity of the allele(s) at the PS is unknown). The specificity of an assay may also be confirmed by comparing the assay result for a test sample with the result obtained for the same sample using a different type of assay, such as by determining the sequence of an amplified target region believed to contain the PS of interest and comparing the determined sequence to context sequences accepted in the art, such as the context sequences provided herein.

The length of the context sequence necessary to establish that the correct genomic position is being assayed will vary based on the uniqueness of the sequence in the target region (for example, there may be one or more highly homologous sequences located in other genomic regions). The skilled artisan can readily determine an appropriate length for a context sequence for any PS using known techniques such as BLASTing the context sequence against publicly available sequence databases. For amplified target regions, which provide a first level of specificity, examining the context sequence of about 30 to 60 bases on each side of the PS in known samples is typically sufficient to ensure that the assay design is specific for the PS of interest. Occasionally, a validated assay may fail to provide an unambiguous result for a test sample. This is usually the result of the sample having DNA of insufficient purity or quantity, and an unambiguous result is usually obtained by repurifying or reisolating the DNA sample or by assaying the sample using a different type of assay.

For detecting PS characterized by an insertion/deletion variations, a number of assay techniques can be employed. Insertion/deletion variants can be detected by Sanger sequencing methods which employ di-deoxynucleosidetriphosphates. In some embodiments, commercially available software packages such as Mutation Surveyor® software available from SoftGenetics LLC, State College, Pennsylvania, USA that can detect homozygous and heterozygous insertion/deletion variants. In addition, the fragment analysis method disclosed in Hjelm et al. in *The Journal of Molecular Diagnostics* 12(5), pp 607-610 (2010) can be used to characterize insertion and deletion variants.

Further, in performing any of the methods described herein that require determining the presence or absence of the TcdB treatment response markers, such determination may be made by consulting a data repository that contains sufficient information on the patient's genetic composition to determine whether the patient has the marker. Preferably, the data repository lists whether the TcdB treatment response markers are present and absent in the individual. The data repository could include the individual's patient records, a medical data card, a file (e.g., a flat ASCII file) accessible by a computer or other electronic or non-electronic media on which appropriate information or genetic data can be stored. As used herein, a medical data card is a portable storage device such as a magnetic data card, a smart card, which has an on-board processing unit and which is sold by vendors such as Siemens of Munich Germany, or a flash-memory card. If the data repository is a file accessible by a computer; such files may be located on various media, including: a server, a client, a hard disk, a CD, a DVD, a personal digital assistant such as a smart phone, a tape, a zip disk, the computer's internal ROM (read-only-memory) or the internet or worldwide web. Other media for the storage of files accessible by a computer will be obvious to one skilled in the art.

The invention also contemplates that testing for the TcdB treatment response markers may be determined by investigating whether the individual has an allele, e.g., a particular nucleotide sequence, at a different locus that is in high linkage disequilibrium (LD) with the better response allele for the rs2516513 SNP, the rs113379306 SNP, the rs76166871 SNP, or one of the other TcdB treatment response markers identified in Table 1 above. Two particular alleles at different loci on the same chromosome are said to be in LD if the presence of one of the alleles at one locus tends to predict the presence of the other allele at the other locus. Such variants, which are referred to herein as "linked variants", or proxy variants, may be any type of variant (e.g., a SNP, insertion or deletion variant) that is in high LD with the better response allele of interest.

Linked variants are readily identified by determining the degree of linkage disequilibrium between the better response allele of the rs2516513 SNP, the rs113379306 SNP, or the rs76166871 SNP, for example, and a candidate linked allele. The candidate linked variant may be an allele of a polymorphism that is currently known. Other candidate linked variants may be readily identified by the skilled artisan using any technique well-known in the art for discovering polymorphisms.

The degree of LD between a better response allele in one of the TcdB treatment response markers, e.g., rs2516513 SNP, the rs113379306 SNP, and/or the rs76166871 SNP, and a candidate linked variant may be determined using any LD measurement known in the art. LD patterns in genomic regions are readily determined empirically in appropriately chosen samples using various techniques known in the art for determining whether any two alleles (e.g., between nucleotides at different PSs) are in linkage disequilibrium (see, e.g., GENETIC DATA ANALYSIS II, Weir, Sineuer Associates, Inc. Publishers, Sunderland, MA 1996). The skilled artisan may readily select which method of determining LD will be best suited for a particular population sample size and genomic region. One of the most frequently used measures of linkage disequilibrium is $r^2$, which is calculated using the formula described by Devlin et al. (*Genomics,* 29(2):311-22 (1995)). $r^2$ is the measure of how well an allele X at a first locus predicts the occurrence of an allele Y at a second locus on the same chromosome. The measure only reaches 1.0 when the prediction is perfect (e.g., X if and only if Y).

In one embodiment, the locus of the linked variant is in a genomic region of about 100 kilobases, more preferably about 10 kb that spans any of the PS of the TcdB treatment response marker of interest, e.g., the rs2516513 SNP, the rs113379306 SNP, the rs76166871 SNP, the HLA-DRB1*07:01 allele, the HLA-DQB1*02:02 allele, or the HLA-DQA1*02:01 allele. Other linked variants are those in which the LD with the better response allele has a $r^2$ value, as measured in a suitable reference population, of at least 0.5, more preferably at least 0.75, even more preferably at least 0.85 or at least 0.90, yet more preferably at least 0.95, and most preferably 1.0. The reference population used for this $r^2$ measurement may be the general population, a population using the TcdB medicament, a population diagnosed CDAD and/or CDI, or a population whose members are self-identified as belonging to the same ethnic group, such as Caucasian, African American, Hispanic, Latino, Native American and the like, or any combination of these categories. Preferably the reference population reflects the genetic diversity of the population of patients to be treated with a TcdB medicament. For example, several $r^2$ values can be observed with the SNPs rs2516513 rs113379306 and rs76166871 in FIGS. 5A, 5B, and 5C. Also, it is also known that there are several HLA alleles that are in High LD with each other, for example HLA-DRB1*07:01 and HLA-DQA1*02:01 are in almost perfect LD with each other ($r^{2=0.98}$) in the GWAS data.

In some embodiments, a health care provider determines whether a patient has the TcdB treatment response marker described herein by ordering a diagnostic test, which is designed to determine whether the patient has at least one copy of the better response allele of one or more of the TcdB treatment response markers in Table 1, e.g., the rs2516513 SNP, the rs113379306 SNP, the rs76166871 SNP, the HLA-DRB1*07:01 allele, the HLA-DQB1*02:02 allele, or the HLA-DQA1*02:01 allele. Preferably, the test determines the identity of both the response allele and the alternative allele, i.e., the genotype, at this PS. In some embodiments, the testing laboratory will prepare a nucleic acid sample from a biological sample (such as a blood sample or buccal swab) obtained from the patient. In some embodiments, a blood sample from the patient is drawn by the health care provider, e.g. physician, or a member of the physician's staff, or by a technician at a diagnostic laboratory. In some embodiments, the patient is provided with a kit for taking a buccal swab from the inside of her cheek, which the patient then gives to the health care provider's staff member or sends directly to the diagnostic laboratory.

In some embodiments, the testing laboratory does not know the identity of the individual whose sample it is testing; i.e., the sample received by the laboratory is made anonymous in some manner before being sent to the laboratory. For example, the sample may be merely identified by a number or some other code (a "sample ID") and the results of the diagnostic method can be reported to the party ordering the test using the sample ID.

In some embodiments, after the test results have been obtained, the testing laboratory generates a test report which indicates whether the better response allele is present or absent at the genotyped polymorphic site, and preferably indicates whether the patient is heterozygous or homozygous for the better response allele. In some embodiments, the test report is a written document prepared by the testing laboratory and sent to the patient or the patient's health care provider as a hard copy or via electronic mail. In other embodiments, the test report is generated by a computer program and displayed on a video monitor in the health care provider's office. The test report may also comprise an oral transmission of the test results directly to the patient or the patient's health care provider, e.g., physician, or an authorized employee in the health care provider's office. Similarly, the test report may comprise a record of the test results that the health care provider makes in the patient's file.

In one embodiment, if the patient tests positive for at least one copy of the better response allele, then the test report further indicates that the patient tested positive for a TcdB treatment response marker, while if the individual tests negative for the better response allele, then the test report further indicates that the patient tested negative for a TcdB treatment response marker.

Typically, the individual would be tested for the presence of a TcdB treatment response marker prior to initiation of the TcdB medicament, e.g. TcdB antibody therapy, but it is envisioned that such testing could be performed at any time after the individual is administered the first dose of the TcdB medicament. For example, the health care provider (e.g. physician or physician's assistant) may be concerned that the patient has not responded adequately and desires to test the individual to determine whether continued treatment with the TcdB medicament is warranted. In some embodiments, a health care provider may determine whether or not an individual should be tested for a TcdB treatment response marker. For example, the health care provider may be considering whether to prescribe to the patient a pharmaceutical product that is indicated for patients who test positive for the TcdB treatment response marker.

In deciding how to use the TcdB treatment response marker test results in treating any individual patient, the health care provider may also take into account other relevant circumstances, whether or not the patient is considered to be at "high risk" of CDI recurrence, the age, weight, gender, genetic background and race of the patient, including inputting a combination of these factors and the genetic marker test results into a model that helps guide the health care provider in choosing a therapy and/or treatment regimen with that therapy.

Detecting the presence or absence of any of the TcdB treatment response markers may be performed using a kit that has been specially designed for this purpose. In one embodiment, a kit of the invention comprises a set of oligonucleotides designed for identifying each of the alleles at the PS, e.g., in the rs2516513 SNP, the rs113379306 SNP, the rs76166871 SNP, the HLA-DRB1*07:01 allele, the HLA-DQB1*02:02 allele, or the HLA-DQA1*02:01 allele.

Accordingly, the invention relates to a kit for testing a patient for the presence or absence of at least one copy of a better response allele of one or more TcdB treatment response markers, wherein the one or more TcdB treatment response markers are selected the group consisting of:
 a) the T allele of the rs2516513 single nucleotide polymorphism (SNP),
 b) the A allele of the rs113379306 SNP,
 c) the A allele of the rs76166871 SNP,
 d) the HLA-DRB1*07:01 allele of the HLA-DRB1 gene,
 e) the HLA-DQB1*02:02 allele of the HLA-DQB1 gene, and
 f) the HLA-DQA1*02:01 allele of the HLA-DQA1 gene;

or a linked variant of the TcdB treatment response marker, wherein the kit comprises one or more sets of oligonucleotides designed to genotype at least one of the TcdB treatment response markers.

In one embodiment of this aspect of the invention, the patient has been diagnosed with a *C. difficile* infection, is suspected of having a *C. difficile* infection, or is exhibiting symptoms of CDAD. In another embodiment, the patient is at high-risk for rCDI.

In a first embodiment of this aspect of the invention, the TcdB treatment response marker is the rs2516513 SNP and the better response allele is the T allele.

In a second embodiment, the TcdB treatment response marker is the rs113379306 SNP and the better response allele is the A allele.

In a third embodiment, the TcdB treatment response marker is the rs76166871 SNP and the better response allele is the A allele.

In a fourth embodiment, the TcdB treatment response marker is the HLA-DRB1 gene and the better response allele is the HLA-DRB1*07:01 allele.

In a fifth embodiment, the TcdB treatment response marker is the HLA-DQB1 gene and the better response allele is the HLA-DQB1*02:02 allele.

In a sixth embodiment, the TcdB treatment response marker is the HLA-DQA1 and the better response allele is the HLA-DQA1*02:01 allele.

In a seventh embodiment, the kit comprises at least two sets of oligonucleotides designed to genotype at least two of the TcdB treatment response markers.

In a sub-embodiment of the seventh embodiment, the at least two TcdB treatment response markers comprise the T allele of the rs2516513 SNP and the HLA-DRB1*07:01 allele of the HLA-DRB1 gene.

In preferred sub-embodiments of any of the above embodiments, the oligonucleotides are allele specific oligonucleotide probes.

As stated above, one aspect of the invention relates to a kit for testing a patient for the presence or absence of at least one copy of a better response allele of one or more TcdB treatment response markers defined above. In sub-embodiments of any of the embodiments described above, the kit comprises one set of oligonucleotides designed to genotype one of the TcdB treatment response markers. If further sub-embodiments, the kit comprises two, three, four, five, six, or more sets of oligonucleotides designed to genotype multiple Tcd treatment response markers of the invention.

In some embodiments, the oligonucleotides in the kit are either allele-specific probes or allele-specific primers. In other embodiments, the kit comprises primer-extension oligonucleotides. In still further embodiments, the set of oligonucleotides is a combination of allele-specific probes, allele-specific primers and primer-extension oligonucleotides. The kit may comprise oligonucleotides designed for detecting the presence of other genetic markers associated with response to a TcdB medicament.

Oligonucleotides in kits of the invention must be capable of specifically hybridizing to a target region of a polynucleotide. As used herein, specific hybridization means the oligonucleotide forms an anti-parallel double-stranded structure with the target region under certain hybridizing conditions, while failing to form such a structure with non-target regions when incubated with the polynucleotide under the same hybridizing conditions. In some embodiments, the target region contains the PS of interest, while in other embodiments, the target region is located one to 10 nucleotides adjacent to the PS.

The composition and length of each oligonucleotide in the kit will depend on the nature of the genomic region containing the PS as well as the type of assay to be performed with the oligonucleotide and is readily determined by the skilled artisan.

For example, the polynucleotide to be used in the assay may constitute an amplification product, and thus the required specificity of the oligonucleotide is with respect to hybridization to the target region in the amplification product rather than in genomic or cDNA isolated from the individual. As another example, if the kit is designed to genotype two or more polymorphic sites simultaneously, the melting temperatures for the oligonucleotides for each PS in the kit will typically be within a narrow range, preferably less than about 5° C. and more preferably less than about 2° C.

In some embodiments, each oligonucleotide in the kit is a perfect complement of its target region. An oligonucleotide is said to be a "perfect" or "complete" complement of another nucleic acid molecule if every nucleotide of one of the molecules is complementary to the nucleotide at the corresponding position of the other molecule. While perfectly complementary oligonucleotides are preferred for detecting polymorphisms, departures from complete complementarity are contemplated where such departures do not prevent the molecule from specifically hybridizing to the target region as defined above. For example, an oligonucleotide primer may have a non-complementary fragment at its 5' end, with the remainder of the primer being completely complementary to the target region. Alternatively, non-complementary nucleotides may be interspersed into the probe or primer as long as the resulting probe or primer is still capable of specifically hybridizing to the target region.

In some preferred embodiments, each oligonucleotide in the kit specifically hybridizes to its target region under stringent hybridization conditions. Stringent hybridization conditions are sequence-dependent and vary depending on the circumstances. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. As the target sequences are generally present in excess, at Tm, 50% of the probes are occupied at equilibrium.

Typically, stringent conditions include a salt concentration of at least about 0.01 to 1.0 M sodium ion concentration (or other salts) at pH 7.0 to 8.3 and the temperature is at least about 25° C. for short oligonucleotide probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. Additional stringent conditions can be found in Molecular Cloning: A Laboratory Manual, Sambrook et al., Cold Spring Harbor Press, Cold Spring Harbor, N.Y. (1989), chapters 7, 9, and 11, and in NUCLEIC ACID HYBRIDIZATION, A PRACTICAL APPROACH, Haymes et al., IRL Press, Washington, D.C., 1985.

One non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70°

C. A non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Stringency conditions with ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete.

The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6($\log_{10}$ [Na+])+0.41(% G+C)−(600/N), where N is the number of bases in the hybrid, and [Na+] is the concentration of sodium ions in the hybridization buffer ([Na+] for 1×SSC=0.165 M).

The oligonucleotides in kits of the invention may be comprised of any phosphorylation state of ribonucleotides, deoxyribonucleotides, and acyclic nucleotide derivatives, and other functionally equivalent derivatives. Alternatively, the oligonucleotides may have a phosphate-free backbone, which may be comprised of linkages such as carboxymethyl, acetamidate, carbamate, polyamide (peptide nucleic acid (PNA)) and the like (Varma, in Molecular Biology and Biotechnology, A Comprehensive Desk Reference, Meyers, ed., pp. 6 17-20, VCH Publishers, Inc., 1995). The oligonucleotides may be prepared by chemical synthesis using any suitable methodology known in the art, or may be derived from a biological sample, for example, by restriction digestion. The oligonucleotides may contain a detectable label, according to any technique known in the art, including use of radiolabels, fluorescent labels, enzymatic labels, proteins, haptens, antibodies, sequence tags and the like. The oligonucleotides in the kit may be manufactured and marketed as analyte specific reagents (ASRs) or may constitute components of an approved diagnostic device.

In some embodiments, the set of oligonucleotides in the kit have different labels to allow simultaneous determination of the identity of the alleles at two or more polymorphic sites. The oligonucleotides may also comprise an ordered array of oligonucleotides immobilized on a solid surface such as a microchip, silica beads (such as BeadArray technology from Illumina, San Diego, CA), or a glass slide (see, e.g., WO 98/20020 and WO 98/20019). Kits comprising such immobilized oligonucleotides may be designed to perform a variety of polymorphism detection assays, including but not limited to probe hybridization and polymerase extension assays.

Kits of the invention may also contain other reagents such as hybridization buffer (e.g., where the oligonucleotides are to be used as allele-specific probes) or dideoxynucleotide triphosphates (ddNTPs; e.g., where the alleles at the polymorphic sites are to be detected by primer extension). Kits designed for use in polymerase-mediated genotyping assays may also contain a polymerase and a reaction buffer optimized for the polymerase-mediated assay to be performed.

Kits of the invention may also include reagents to detect when a specific hybridization has occurred or a specific polymerase-mediated extension has occurred. Such detection reagents may include biotin- or fluorescent-tagged oligonucleotides or ddNTPs and/or an enzyme-labeled antibody and one or more substrates that generate a detectable signal when acted on by the enzyme.

It will be understood by the skilled artisan that the set of oligonucleotides and reagents for performing the assay will be provided in separate receptacles placed in the kit container if appropriate to preserve biological or chemical activity and enable proper use in the assay.

In other embodiments, each of the oligonucleotides and all other reagents in the kit have been quality tested for optimal performance in an assay designed to determine the genotype for at least one or more of the PS in Table 1 above, e.g., the rs2516513 SNP, the rs113379306 SNP, the rs76166871 SNP, the HLA-DRB1*07:01 allele of the HLA-DRB1 gene, the HLA-DQB1*02:02 allele of the HLA-DQB1 gene, or the HLA-DQA1*02:01 allele of the HLA-DQA1 gene. In some embodiments, the kit includes an instruction manual that describes how to use the determined genotype to assign, to the tested nucleic acid sample, the presence or absence of a response marker.

In some preferred embodiments, the set of oligonucleotides in the kit are allele-specific oligonucleotides. As used herein, the term allele-specific oligonucleotide (ASO) means an oligonucleotide that is able, under sufficiently stringent conditions, to hybridize specifically to one allele of a PS, at a target region containing the PS while not hybridizing to the same region containing a different allele. As understood by the skilled artisan, allele-specificity will depend upon a variety of readily optimized stringency conditions, including salt and formamide concentrations, as well as temperatures for both the hybridization and washing steps.

Examples of hybridization and washing conditions typically used for ASO probes and primers are found in Kogan et al., "Genetic Prediction of Hemophilia A" in PCR Protocols, A Guide to Methods and Applications, Academic Press, 1990, and Ruaflo et al., *Proc. Natl. Acad. Sci. USA* 87:6296-300 (1990).

Typically, an ASO will be perfectly complementary to one allele while containing a single mismatch for the other allele. In ASO probes, the single mismatch is preferably within a central position of the oligonucleotide probe as it aligns with the polymorphic site in the target region (e.g., approximately the 7th or 8th position in a 15mer, the 8th or 9th position in a 16mer, and the 10th or 11th position in a 20mer). The single mismatch in ASO primers is located at the 3' terminal nucleotide, or preferably at the 3' penultimate nucleotide. ASO probes and primers hybridizing to either the coding or noncoding strand are contemplated by the invention.

In some embodiments, the kit comprises a pair of allele-specific oligonucleotides for each PS to be assayed, with one member of the pair being specific for one allele (e.g., the better response allele) and the other member being specific for the other allele. In such embodiments, the oligonucleotides in the pair may have different lengths or have different detectable labels to allow the user of the kit to determine the genotype for the assayed PS.

In still other preferred embodiments, the oligonucleotides in the kit are primer-extension oligonucleotides. Termination mixes for polymerase-mediated extension from any of these oligonucleotides are chosen to terminate extension of the oligonucleotide at the PS of interest, or one base thereafter, depending on the alternative nucleotides present at the PS.

In another embodiment, the kit comprises a pair of allele specific oligonucleotide probes for genotyping at least one of the polymorphic sites in Table 1. In one embodiment, one ASO probe in the pair comprises a nucleotide sequence of at least 15 nucleotides that is identical to or perfectly complementary to the better response allele of the context sequence shown in Table 2 and the other ASO probe in the pair comprises a nucleotide sequence of at least 15 nucleotides that is identical to or perfectly complementary to the other allele of the context sequence shown in Table 2.

In another embodiment, the kit comprises a pair of ASO probes comprising a first and a second ASO probe for genotyping the rs2516513 SNP, the rs113379306 SNP, or the rs76166871 SNP. In one embodiment, the first ASO probe in the pair comprises a nucleotide sequence of at least 15 nucleotides that is identical to or perfectly complementary to the better response allele of the rs2516513 SNP, the rs113379306 SNP, or the rs76166871 SNP, and the second ASO probe in the pair comprises a nucleotide sequence of at least 15 nucleotides that is identical to or perfectly complementary to the other allele of the rs2516513 SNP, the rs113379306 SNP, or the rs76166871 SNP.

In another embodiment, the kit comprises two or more pairs of ASO probes. In particular embodiments, the kit comprises one pair of ASO probes for genotyping the rs2516513 SNP and a second pair of ASO probes for genotyping the rs113379306 SNP. In another embodiment the kit comprises one pair of ASO probes for genotyping the rs2516513 SNP and a second pair of ASO probes for genotyping the rs76166871 SNP. In a further embodiment, the kit comprises one pair of ASO probes for genotyping the rs113379306 SNP and a second pair of ASO probes for genotyping the rs76166871 SNP. In an additional embodiment, the kit comprises one pair of ASO probes for genotyping the rs2516513 SNP, a second pair of ASO probes for genotyping the rs113379306 SNP and a third pair of ASO probes for genotyping the rs76166871 SNP.

In another embodiment, the kit comprises a pair of allele specific oligonucleotide probes for genotyping the HLA-DRB1*07:01 allele. In one embodiment, one ASO probe in the pair comprises a nucleotide sequence of at least 15 nucleotides that is identical to or perfectly complementary to the better response HLA-DRB1*07:01 allele and the other ASO probe in the pair comprises a nucleotide sequence of at least 15 nucleotides that: (1) is identical to or perfectly complementary to a different allele of the HLA-DRB1 gene, e.g., an allele of the HLA-DRB1 gene that is common in the population being tested or (2) does not hybridize to the HLA-DRB1*07:01 allele under high stringency conditions, but binds to more than one different allele of the HLA-DRB1 gene, e.g., a consensus oligonucleotide sequence. In another embodiment, the kit comprises an ASO probe that is identical to or perfectly complementary to the better response HLA-DRB1*07:01 allele, and a cocktail comprising two or more ASO probes that bind to more than one different allele of the HLA-DRB1 gene. In an alternative embodiment, one ASO probe in the pair comprises a nucleotide sequence of at least 15 nucleotides that is identical to or perfectly complementary to the better response HLA-DRB1*07:01 allele and the other ASO probe in the pair comprises a nucleotide sequence of at least 15 nucleotides that is a control sequence, i.e. a positive or negative control.

In another embodiment, the kit comprises a pair of allele specific oligonucleotide probes for genotyping the HLA-DQB1*02:02 allele. In one embodiment, one ASO probe in the pair comprises a nucleotide sequence of at least 15 nucleotides that is identical to or perfectly complementary to the better response HLA-DQB1*02:02 allele and the other ASO probe in the pair comprises a nucleotide sequence of at least 15 nucleotides that: (1) is identical to or perfectly complementary to a different allele of the HLA-DQB1 gene, e.g. an allele of the HLA-DQB1 gene that is common in the population being tested, or (2) does not hybridize to the HLA-DQB1*02:02 allele under high stringency conditions, but binds to more than one different allele of the HLA-DQB1 gene, e.g. a consensus oligonucleotide sequence. In another embodiment, the kit comprises one ASO probe that is identical to or perfectly complementary to the better response HLA-DQB1*02:02 allele, and a cocktail comprising two or more ASO probes that bind to more than one different allele of the HLA-DRB1 gene. In an alternative embodiment, one ASO probe in the pair comprises a nucleotide sequence of at least 15 nucleotides that is identical to or perfectly complementary to the better response HLA-DQB1*02:02 allele and the other ASO probe in the pair comprises a nucleotide sequence of at least 15 nucleotides that is a control sequence; i.e. a positive or negative control.

In another embodiment, the kit comprises a pair of allele specific oligonucleotide probes for genotyping the HLA-DQA1*02:01 allele. In one embodiment, one ASO probe in the pair comprises a nucleotide sequence of at least 15 nucleotides that is identical to or perfectly complementary to the better response HLA-DQA1*02:01 allele and the other ASO probe in the pair comprises a nucleotide sequence of at least 15 nucleotides that: (1) is identical to or perfectly complementary to a different allele of the HLA-DQA1 gene, e.g. an allele of the HLA-DQA1 gene that is common in the population being tested, or (2) does not hybridize to the HLA-DQA1*02:01 allele, but binds to more than one different allele of the HLA-DQA1 gene, e.g. a consensus oligonucleotide sequence. In another embodiment, the kit comprises one ASO probe that is identical to or perfectly complementary to the better response HLA-DQA1*02:01 allele, and a cocktail comprising two or more ASO probes that bind to more than one different allele of the HLA-DQA1 gene. In an alternative embodiment, one ASO probe in the pair comprises a nucleotide sequence of at least 15 nucleotides that is identical to or perfectly complementary to the better response HLA-DQA1*02:01 allele and the other ASO probe in the pair comprises a nucleotide sequence of at least 15 nucleotides that is a control sequence, i.e. a positive or negative control.

In further embodiments of any of the kits described above, the ASO probe that binds to the HLA-DRB1*07:01 allele, the HLA-DQB1*02:02 allele, or the HLA-DQA1*02:01 allele, is not identical to or perfectly complementary to the better response HLA-DRB1*07:01 allele, but comprises a nucleotide sequence of at least 15 nucleotides that is highly homologous to the HLA-DRB1*07:01 allele or highly homologous to the complement of the HLA-DRB1*07:01 allele. By "highly homologous", it is intended that the probe has sufficient homology with the target sequence to specifically bind, i.e. hybridize, to the target sequence under high stringency conditions.

In some embodiments of any of the kits of the invention described above, the kit comprises one set of ASO probes for detecting the rs2516513 SNP, the rs113379306 SNP, the rs76166871 SNP, HLA-DRB1*07:01 allele, the HLA-DQB1*02:02 allele, or the HLA-DQA1*02:01 allele. In further embodiments, the kit comprises two, three, four, five, six, or more sets of ASO probes for detecting more than one of the TcdB treatment response markers of the invention, or linked variants of the TcdB treatment response markers.

Pharmaceutical Compositions, Drug Products and Treatment Regimens

In one aspect, the invention provides a method of preventing the recurrence of a *Clostridium difficile* (*C. difficile*) infection comprising: administering a therapeutically effective amount of a treatment that targets *C. difficile* toxin B (TcdB treatment, alternatively TcdB medicament) to a patient in need thereof, wherein said patient, prior to the administration of the TcdB treatment, has tested positive for at least one copy of a better response allele from one or more TcdB treatment response markers, or linked variants; wherein the one or more TcdB treatment response marker is selected from the group consisting of: (a) the T allele of the rs2516513 single nucleotide polymorphism (SNP); (b) the A allele of the rs113379306 SNP; (c) the A allele of the rs76166871 SNP; (d) the HLA-DRB1*07:01 allele of the HLA-DRB1 gene; (e) the HLA-DQB1*02:02 allele of the HLA-DQB1 gene; and (f) the HLA-DQA1*02:01 allele of the HLA-DQA1 gene.

In a first embodiment of the method described above (Embodiment E1), the treatment that targets TcdB is a TcdB antibody or an antigen binding fragment thereof.

In a second embodiment of the method described above (Embodiment E2), the treatment that targets TcdB is a small molecule drug product.

In a third embodiment of the method described above (Embodiment E3), the treatment that targets TcdB is a TcdB antibody, or antigen binding fragment thereof, which comprises three heavy chain CDRs (CDRH1, CDRH2, and CDRH3) and three light chain CDRs (CDRL1, CDRL2, and CDRL3), wherein:
  a) CDRH1 consists of the amino acid sequence set forth in SEQ ID NO:7, or is a variant of SEQ ID NO:7 having one or two conservative amino acid substitutions;
  b) CDRH2 consists of the amino acid sequence set forth in SEQ ID NO:8, or is a variant of SEQ ID NO:8 having one or two conservative amino acid substitutions;
  c) CDRH3 consists of the amino acid sequence set forth in SEQ ID NO:9, or is a variant of SEQ ID NO:9 having one or two conservative amino acid substitutions;
  d) CDRL1 consists of the amino acid sequence set forth in SEQ ID NO:2, or is a variant of SEQ ID NO:2 having one or two conservative amino acid substitutions;
  e) CDRL2 consists of the amino acid sequence set forth in SEQ ID NO:3, or is a variant of SEQ ID NO:3 having one or two conservative amino acid substitutions; and
  f) CDRL3 consists of the amino acid sequence set forth in SEQ ID NO:4, or is a variant of SEQ ID NO:4 having one or two conservative amino acid substitutions.

In a fourth embodiment of the method described above (Embodiment E4), the treatment that targets TcdB is a TcdB antibody, or antigen binding fragment thereof, which comprises a variable heavy region comprising an amino acid sequence as set forth in SEQ ID NO:5 and a light chain variable region comprising an amino acid sequence as set forth in SEQ ID NO:1.

In a fifth embodiment of the method described above (Embodiment E5), the treatment that targets TcdB is bezlotoxumab.

In a sixth embodiment of the method described above (Embodiment E6), the treatment that targets TcdB is as set forth in any of Embodiments E1-E5 and the patient is a human patient who, prior to administration of the TcdB treatment, has tested positive for CDI.

In a seventh embodiment of the method described above (Embodiment E7), the treatment that targets TcdB is as set forth in any of Embodiments E1-E5 and the patient is a human patient who, prior to administration of the TcdB treatment, is suspected of having CDI or exhibits symptoms of CDAD; or was suspected of having CDI or had exhibited symptoms of CDAD.

In an eighth embodiment of the method described above (Embodiment E8), the treatment that targets TcdB is as set forth in any of Embodiments E1-E5, the patient is as set forth in Embodiments E6 or E7; and the TcdB treatment response marker comprises one or more TcdB treatment response markers selected from the group consisting of: (a) the T allele of the rs2516513 SNP; (b) the A allele of the rs113379306 SNP; (c) the A allele of the rs76166871 SNP; (d) the HLA-DRB1*07:01 allele of the HLA-DRB1 gene; (e) the HLA-DQB1*02:02 allele of the HLA-DQB1 gene; and (f) the HLA-DQA1*02:01 allele of the HLA-DQA1 gene.

In a ninth embodiment of the method described above (Embodiment E9), the treatment that targets TcdB is as set forth in any of Embodiments E1-E5, the patient is as set forth in Embodiments E6 or E7; and the TcdB treatment response marker comprises the T allele of the rs2516513 SNP, or a linked variant.

In a tenth embodiment of the method described above (Embodiment E10), the treatment that targets TcdB is as set forth in any of Embodiments E1-E5, the patient is as set forth in Embodiments E6 or E7; and the TcdB treatment response marker comprises the A allele of the rs113379306 SNP, or a linked variant.

In an eleventh embodiment of the method described above (Embodiment E11), the treatment that targets TcdB is as set forth in any of Embodiments E1-E5, the patient is as set forth in Embodiments E6 or E7; and the TcdB treatment response marker comprises the A allele of the rs76166871 SNP, or a linked variant.

In a twelfth embodiment of the method described above (Embodiment E12), the treatment that targets TcdB is as set forth in any of Embodiments E1-E5, the patient is as set forth in Embodiments E6 or E7; and the TcdB treatment response marker comprises the HLA-DRB1*07:01 allele of the HLA-DRB1 gene, or a linked variant.

In a thirteenth embodiment of the method described above (Embodiment E13), the treatment that targets TcdB is as set forth in any of Embodiments E1-E5, the patient is as set forth in Embodiments E6 or E7; and the TcdB treatment response marker comprises the HLA-DQB1*02:02 allele of the HLA-DQB1 gene, or a linked variant.

In a fourteenth embodiment of the method described above (Embodiment E14), the treatment that targets TcdB is as set forth in any of Embodiments E1-E5, the patient is as set forth in Embodiments E6 or E7; and the TcdB treatment response marker comprises the HLA-DQA1*02:01 allele of the HLA-DQA1 gene, or a linked variant.

In a fifteenth embodiment of the method described above (Embodiment E15), the treatment that targets TcdB is as set forth in any of Embodiments E1-E5, the patient is as set forth in Embodiments E6 or E7; and the TcdB treatment response marker comprises both the T allele of the rs2516513 SNP and the HLA-DRB1*07:01 allele of the HLA-DRB1 gene.

In a sixteenth embodiment of the method described above (Embodiment E16), the treatment that targets TcdB is as set forth in any of Embodiments E1-E5, the patient is as set forth in Embodiments E6 or E7; and the TcdB treatment response marker comprises more than one of the TcdB treatment response markers set forth in Table 1, or linked variants.

In a further embodiment of any of the methods and Embodiments described above (e.g. Embodiment E1-E16), the method further comprises treating said patient with an antibiotic that is effective against *C. difficile* infection.

In a further embodiments of any of the methods and Embodiments described above (e.g. Embodiment E1-E16), the patient is a high-risk patient.

In some embodiments, the antibiotic is selected from the group consisting of vancomycin, metronidazole and fidaxomicin.

In sub-embodiments of any of the Embodiments described above, the patient tests positive for one copy of a better response allele of one or more TcdB treatment response markers of the invention, or linked variants. In alternative sub-embodiments, the patients tests positive for two copies of a better response allele of one or more TcdB treatment response markers of the invention, or linked variants.

The invention further provides a method of determining if a patient is likely to respond to a medicament that targets *C. difficile* toxin B (TcdB) in a human patient, said method comprising: (a) obtaining or having obtained a biological sample from said patient; (b) determining whether a better response allele of at least one TcdB response marker, or a linked variant, is present in the biological sample, wherein the TcdB response marker is selected from the group consisting of: (i) the T allele of the rs2516513 single nucleotide polymorphism (SNP); (ii) the A allele of the rs113379306 SNP; (iii) the A allele of the rs76166871 SNP; (iv) the HLA-DRB1*07:01 allele of the HLA-DRB1 gene; (v) the HLA-DQB1*02:02 allele of the HLA-DQB1 gene; and (vi) the HLA-DQA1*02:01 allele of the HLA-DQA1 gene; and (c) diagnosing the patient as susceptible to treatment with a TcdB medicament when the presence of the better response allele in the biological sample is detected.

In some embodiments of the invention above, the method further comprises step (d), which comprises administering a therapeutically effective amount of the TcdB medicament to the diagnosed patient.

In one embodiment of the method above, the TcdB medicament is a TcdB antibody, or antigen binding fragment thereof. In specific embodiments, the TcdB antibody or antigen binding fragment thereof is bezlotoxumab.

In additional embodiments, the method further comprises administering an antibiotic that is effective against *Clostridium difficile* infection to the patient. In specific embodiments, the antibiotic is selected from the group consisting of vancomycin, metronidazole and fidaxomicin.

In some embodiments of any of the methods above, in step (b), the T allele of the rs2516513 SNP or the HLA-DRB1*07:01 allele of the HLA-DRB1 gene is detected, and in step (c), the patient is diagnosed as susceptible to treatment with a TcdB antibody when the T allele of the rs2516513 SNP or the HLA-DRB1*07:01 allele of the HLA-DRB1 gene is detected or if both the rs2516513 SNP and the HLA-DRB1*07:01 allele of the HLA-DRB1 gene are detected.

In embodiments of the method of determining above, the patient is a human who has been diagnosed with a *Clostridium difficile* infection, or exhibits symptoms of *Clostridium-difficile* associated disease. In specific embodiments, the patient is an adult human.

In embodiments of the method of determining above, step (b) comprises sending the biological sample to a diagnostic laboratory to determine if a better response allele of the TcdB treatment response marker is present in the sample.

The invention also relates to a drug product which comprises a pharmaceutical composition and prescribing information, wherein the pharmaceutical composition comprises a TcdB antibody and the prescribing information comprises a pharmacogenetic indication, wherein the pharmacogenetic indication comprises treatment of *C. difficile* infection or the prevention of *C. difficile* recurrence in patients infected with *C. difficile* who test positive for at least one copy of a better response allele selected from a TcdB treatment response marker, or a linked variant, selected from the group consisting of: (a) the T allele of the rs2516513 single nucleotide polymorphism (SNP); (b) the A allele of the rs113379306 SNP; (c); the A allele of the rs76166871 SNP; (d) the HLA-DRB1*07:01 allele of the HLA-DRB1 gene; (e) the HLA-DQB1*02:02 allele of the HLA-DQB1 gene; and (f) the HLA-DQA1*02:01 allele of the HLA-DQA1 gene.

In embodiments of this aspect of the invention, the TcdB antibody response marker is the T allele of the rs2516513 SNP and/or the HLA-DRB1*07:01 allele of the HLA-DRB1 gene.

In further embodiments of the drug product of the invention, the pharmacogenetic indication further comprises treatment of the *C. difficile* infection with an antibiotic. In specific embodiments, the antibiotic is selected from the group consisting of: vancomycin, metronidazole and fidaxomicin.

In some embodiments of any of the drug products of the invention, the TcdB antibody is a bezlotoxumab.

The invention also provides bezlotoxumab for use in preventing *C. difficile* recurrence in a subgroup of patients that have tested positive for a better response allele of a TcdB treatment response marker selected from the group consisting of: (a) the T allele of the rs2516513 SNP; (b) the A allele of the rs113379306 SNP; (c) the A allele of the rs76166871 SNP (d) the HLA-DRB1*07:01 allele of the HLA-DRB1 gene; (e) the HLA-DQB1*02:02 allele of the HLA-DQB1 gene; and (f) the HLA-DQA1*02:01 allele of the HLA-DQA1 gene; or a linked variant of the TcdB treatment response marker.

Further provided by the invention is the use of bezlotoxumab in the manufacture of a medicament for the prevention of *C. difficile* recurrence in a human patient, wherein the patient has tested positive for a better response allele of a TcdB treatment response marker selected from the group consisting of (a) the T allele of the rs2516513 SNP; (b) the A allele of the rs113379306 SNP; (c) the A allele of the rs76166871 SNP (d) the HLA-DRB1*07:01 allele of the HLA-DRB1 gene; (e) the HLA-DQB1*02:02 allele of the HLA-DQB1 gene; and (f) the HLA-DQA1*02:01 allele of the HLA-DQA1 gene; or a linked variant of the TcdB treatment response marker.

In some embodiments of the use above, the better response allele of the TcdB treatment response marker is the T allele of the rs2516513 SNP or the HLA-DRB1*07:01 allele of the HLA-DRB1 gene. In additional embodiments of the use above, the patient has tested positive for both the T allele of the rs2516513 SNP and the HLA-DRB1*07:01 allele of the HLA-DRB1 gene.

In some embodiments, the TcdB medicament used in the pharmaceutical compositions, drug products, kits, methods, and uses of the present invention may be any known TcdB medicament, such as an antibody. In one embodiment, the TcdB medicament is a TcdB antibody. In some preferred embodiments, the TcdB antibody is bezlotoxumab. In additional embodiments, the TcdB antibody is an antibody that specifically binds to TcdB, or an antigen binding fragment thereof, which comprises light chain CDRs (CDRL1, CDRL2, and CDRL3) consisting of a sequence of amino acids as set forth in SEQ ID NOs: 2, 3, and 4, respectively, and heavy chain CDRs (CDRH1, CDRH2, and CDRH3) consisting of a sequence of amino acids as set forth in SEQ ID NOs: 6, 7, and 8, respectively. In further embodiments, the TcdB antibody is an antibody that specifically binds to TcdB, or an antigen binding fragment thereof, which comprises a $V_L$ region comprising a sequence of amino acids as set forth in SEQ ID NO:1 and a $V_H$ region comprising a sequence of amino acids as set forth in SEQ ID NO:5.

In some embodiments of the methods and uses of the invention, the TcdB antibody is administered in combination with an antibiotic. In further embodiments, the TcdB antibody is administered in combination with an antibiotic selected from the group consisting of: vancomycin, metronidazole and fidaxomicin. The TcdB antibody and the antibiotic can be administered in the same or separate dosage forms.

Disorders that may be treated with the pharmaceutical compositions, drug products, kits, methods, and uses of the present invention in accordance with the present invention are generally those that are susceptible to treatment with a TcdB medicament, i.e., the TcdB antibody achieves a clinically measurable beneficial result in a group of patients with the disease. Exemplary diseases and conditions susceptible to treatment with a TcdB medicament include antibiotic-associated diarrhea, colitis, and pseudomembranous colitis and/or *C. difficile* infection.

In certain embodiments, the present invention provides a pharmaceutical composition, drug product, kit, method, or use for treating *C. difficile* infection which include instructions for administering a therapeutically effective dose of a TcdB antibody to a patient in need of such treatment. In a specific embodiment, the disease or condition being treated is *C. difficile* infection. In further embodiments, the patient is exhibiting symptoms of CDAD.

In preferred embodiments, a TcdB antibody response marker of the present invention is used in conjunction with any a TcdB antibody monotherapy or combination therapy treatment regimen comprising a TcdB antibody and an antibiotic. In specific embodiments, the antibiotic is selected from the group consisting of metronidazole, vancomycin, and fidaxomicin.

The doses and dosage regimen of the other agents used in the combination therapies of the present invention for the treatment of disorders susceptible to treatment by a TcdB antibody can be determined by the attending clinician, taking into consideration the approved doses and dosage regimen in the package insert; and the age, sex and general health of the patient. Agents administered in combination therapy can be administered simultaneously (i.e., in the same composition or in separate compositions one right after the other) or sequentially. This is particularly useful when the components of the combination are given on different dosing schedules, e.g., one component is administered once daily and another is given once weekly, or when the preferred pharmaceutical compositions are different, e.g., one is a tablet and one is a capsule or infusion. A kit comprising the separate dosage forms is therefore advantageous.

When administering a combination therapy that is selected to treat a patient based on the presence or absence of a TcdB treatment response marker in the patient, the therapeutic agents in the combination, or a pharmaceutical composition or compositions comprising the therapeutic agents, may be administered in any order such as, for example, sequentially, concurrently, together, simultaneously and the like. The amounts of the various therapeutic agents in such combination therapy may be different amounts (different dosage amounts) or same amounts (same dosage amounts). In some embodiments, the agents in the combination are administered in doses commonly employed when such agents are used as monotherapy for treating the patient's disease or condition, while in other embodiments, the agents are administered in doses lower than the doses commonly employed when such agents are used as monotherapy for treating the disease or condition.

The inventors herein also contemplate that the TcdB treatment response markers described herein could be used to seek regulatory approval to market a new TcdB medicament or TcdB antibody for a pharmacogenetic indication, i.e., an indication that includes a disease component and a TcdB treatment marker component. The disease component is a disease susceptible to treatment with the TcdB medicament such as CDI and the genetic marker component is a patient who tests positive for at least one copy of one of the better response alleles as set forth in Table 1 (e.g., for at least one of one copy of the T allele of the rs2516513 SNP). Similarly, the inventors herein contemplate that the TcdB treatment response markers are useful for seeking approval of such pharmacogenetic indications for currently approved TcdB medicament or TcdB antibodies that health care providers are reluctant to prescribe for certain diseases based on the marginal benefit/risk ratio of the drug for such diseases in the general population.

Seeking approval for a pharmacogenetic indication can involve measuring the incidence of a desired response to a drug in two separate groups of patients treated with the drug. Each individual within one of the groups has disease and genetic profiles that place the individual within the proposed pharmacogenetic indication. The individuals in the other group may be randomly selected without regard to whether they have the genetic marker component of the proposed pharmacogenetic indication. Alternately, the individuals are assigned to the other group in a manner that results in a "control" group in which the percentage of individuals who meet and do not meet the genetic marker component is similar to what is observed in the general population, or in a population of patients with the disease component of the proposed pharmacogenetic indication. The drug product for which approval is sought could be administered to the two groups in a prospective trial. Alternatively, a retrospective pharmacogenetic analysis of patients previously treated with the drug could be performed. One of skill in the art can readily determine an alternative study design to test a particular pharmacogenetic indication of interest.

The drug product for which a pharmacogenetic indication is being sought could be evaluated with other therapeutically active agents, for example another drug with efficacy for treating the disease or condition in the proposed pharmacogenetic indication or an agent that is intended to reduce the incidence of an adverse effect caused by the drug. In some embodiments, the pharmacogenetic indication for which regulatory approval is sought may include other markers (genetic markers or biomarkers) or predictors of response to the drug.

The pharmacogenetic study could be designed in consultation with representatives of the regulatory agency or government entity from whom approval is required before marketing the pharmacogenetic drug product in a particular country. Preferably, the regulatory agency is authorized by the government of a major industrialized country, such as Australia, Canada, China, a member of the European Union, Japan, South Korea, Taiwan or the like. Most preferably the regulatory agency is authorized by the government of the United States and the type of application for approval that is filed will depend on the legal requirements set forth in the last enacted version of the Food, Drug and Cosmetic Act that are applicable for the drug product and may also include other considerations such as the cost of making the regulatory filing and the marketing strategy for the drug product. For example, if the pharmaceutical formulation in the drug product has previously been approved for the disease component of the proposed pharmacogenetic indication, then the application might be a paper NDA or an application filed under section 351(k) of the Public Health services Act, a supplemental NDA or BLA or an abbreviated NDA or BLA, but the application might need to be a full NDA or BLA if the pharmaceutical formulation has never been approved before; with these terms having the meanings applied to them by those skilled in the pharmaceutical arts or as defined in the Drug Price Competition and Patent Term Restoration Act of 1984 or the Biologics Price Competition and Innovation Act of 2009 (BPCIA) of the Patient Protection and Affordable Care Act (2010).

One desired outcome of a pharmacogenetic clinical trial using the TcdB treatment response marker of the invention is approval to market a drug product which comprises (1) a TcdB medicament pharmaceutical composition and (2) prescribing information which includes a pharmacogenetic indication for which the pharmaceutical composition is recommended. Prescribing information is typically found in the product insert, also frequently referred to as the package insert or label, for the drug.

As discussed above, the pharmacogenetic indication has two components: a disease component and the TcdB treatment response marker component. Thus, the prescribing information would describe a genetically defined group of patients for which the drug has demonstrated efficacy for one or more diseases, symptoms or medical conditions. In some embodiments, the prescribing information will discuss how to identify individuals who are in the genetically defined group. For example, in some embodiments, the prescribing information states that the drug is indicated for individuals who test positive for the better response allele of a TcdB antibody response marker described herein. Alternately, the prescribing information may state that the drug is contraindicated for individuals who test negative for a better response allele of a TcdB antibody response marker described herein. In other embodiments, the approved labeling may state that the TcdB medicament is indicated for prevention of recurrence of CDI in patients who carry a particular genotype of a TcdB treatment response marker, e.g., patients who are homozygous (T/T) or heterozygous (C/T) at the rs2516513 SNP, or patients who carry a better response allele of another TcdB treatment response marker set forth herein. In some preferred embodiments, the prescribing information includes the name of at least one approved diagnostic test to be used for detecting the presence or absence of the required genetic marker component of the pharmacogenetic indication. As described above, a pharmacogenetic indication in a pharmacogenetic drug product of the invention may include additional markers or predictors of response to the TcdB medicament pharmaceutical composition and/or a requirement to use the drug in combination with one or more other therapeutically active agents (e.g., antibiotics). The prescribing information may include information on recommended dosages and treatment regimens.

In preferred pharmacogenetic drug products of the invention, the pharmaceutical composition comprises a TcdB medicament. In preferred embodiments of this aspect of the invention, the TcdB medicament is a TcdB antibody. In a further preferred embodiment, the TcdB antibody is bezlotoxumab. In additional embodiments, the TcdB antibody is an antibody that specifically binds to TcdB, or an antigen binding fragment thereof, which comprises light chain CDRs (CDRL1, CDRL2, and CDRL3) consisting of a sequence of amino acids as set forth in SEQ ID NOs: 2, 3, and 4, respectively, and heavy chain CDRs (CDRH1, CDRH2, and CDRH3) consisting of a sequence of amino acids as set forth in SEQ ID NOs: 6, 7, and 8, respectively. In further embodiments, the TcdB antibody is an antibody that specifically binds to TcdB, or an antigen binding fragment thereof, which comprises a $V_L$ region comprising a sequence of amino acids as set forth in SEQ ID NO:1 and a $V_H$ region comprising a sequence of amino acids as set forth in SEQ ID NO:5.

A preferred pharmacogenetic indication for the drug products of the invention comprises the use of the pharmaceutical composition for the treatment of patients suffering from *C. difficile* infection and at least one copy of one of the better response alleles for the TcdB antibody response markers set forth in Table 1. In preferred embodiments, the patients test positive for at least one copy of the T allele for the rs2516513 SNP. In some embodiments, the prescribing information states that the TcdB antibody pharmaceutical composition is indicated in combination with an antibiotic (e.g., vancomycin, metronidazole or fidaxomicin) for treating patients suffering from *C. difficile* infection.

Any or all analytical and mathematical operations involved in performing the methods and uses described herein or in using the kits, composition and drug products described herein may be implemented by a computer. For example, the computer may execute a computer program that assigns the presence or absence of the better response allele of the TcdB antibody response marker to an individual based on genotype data inputted by an employee of a testing laboratory or by the treating health care provider. In addition, the same computer or a different computer may output the predicted response to TcdB antibody therapy based on that response marker assignment. Data relating to the presence or absence of the better response allele of a TcdB antibody response marker in an individual may be stored as part of a relational database (e.g., an instance of an Oracle database or a set of ASCII flat files) containing other clinical and/or genetic data for the individual. These data may be stored on the computer's hard drive or may, for example, be stored on a CD ROM or on one or more other storage devices accessible by the computer. For example, the data may be stored on one or more databases in communication with the computer via a network.

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

Clinical Trials of Actoxumab/Bezlotoxumab and Bezlotoxumab in Subjects with CDI

In order to identify genetic contributions to treatment response, the inventors conducted a pharmacogenetic (PGx) analysis on *C. difficile* infected subjects who had undergone a clinical trial with an antibody to *C. difficile* toxin B to assess whether the mean treatment difference varies across patient subgroups defined by genetic variants using a genome wide association study (GWAS) approach. The Clinical Study design of the two clinical trials, referred to as MODIFY I (PN001) and MODIFY II (PN002), is depicted in FIG. 1.

PN001, was an adaptive-design Phase 3 trial, and subjects with confirmed CDI and receiving standard of care treatment for CDI (metronidazole, vancomycin, or fidaxomicin) were randomized in a 1:1:1:1 ratio into 1 of 4 treatment groups (bezlotoxumab, actoxumab, actoxumab/bezlotoxumab, or placebo). At the pre-specified interim analysis, the actoxumab arm was stopped, a decision driven by both low efficacy and observed increase in the number of deaths and serious adverse events ("SAEs") relative to placebo. Overall, a total of 1412 patients with confirmed CDI were randomized and received study medication: 390 in bezlotoxumab, 235 in actoxumab, 387 in actoxumab/bezlotoxumab, and 400 in placebo groups. PN001 met the primary efficacy objective demonstrating that treatment with bezlotoxumab significantly decreases the proportion of subjects with CDI recurrence over 12 weeks as compared to treatment with placebo (one-sided $p=0.0003$). CDI recurrence rates were 17.4% in the bezlotoxumab and 27.6% in the placebo groups. For actoxumab/bezlotoxumab group, the CDI recurrence rate was 15.9% and was significantly (one sided $p<0.0001$) better than placebo, but was not significantly better than bezlotoxumab ($p=0.2997$). Hence, addition of actoxumab/bezlotoxumab to therapy (i.e., actoxumab/bezlotoxumab) did not have efficacy benefit over bezlotoxumab alone. The reduction in CDI recurrence rate for the bezlotoxumab group versus placebo was also observed in pre-specified subgroups of subjects at high risk for recurrence and/or CDI-related adverse outcomes (i.e., patients ≥65 years of age, with a history of CDI in past 6 months before the baseline episode, clinically severe CDI, 027 ribotype, epidemic strain, or compromised immunity). Although there was a numerical difference favoring the bezlotoxumab treatment group (60.1%) over placebo (55.2%) with respect to the key secondary endpoint of global cure (also known as sustained clinical response), statistical significance was not attained ($p=0.0861$). Actoxumab/bezlotoxumab did not have an advantage over bezlotoxumab (one-sided $p=0.6532$) for the global cure endpoint either (58.7% for actoxumab/bezlotoxumab, 60.1% for bezlotoxumab). PN002 was identical to PN001 in design and conduct, with the following 3 exceptions: PN002 contained 3 treatment groups (bezlotoxumab, actoxumab/bezlotoxumab, and placebo), was a traditional clinical trial of fixed design, and had an extended 9 months follow-up of a subset of subjects (~300) to assess CDI recurrence and colonization with toxigenic *C. difficile*. All other design features were identical between PN001 and PN002. A total of 1167 patients with confirmed CDI were randomized and received study medication: 396 in bezlotoxumab, 390 in actoxumab/bezlotoxumab, and 381 in placebo groups. PN002 also met the primary efficacy objective and confirmed that treatment with bezlotoxumab significantly decreases the proportion of subjects with CDI recurrence over a period of 12 weeks as compared to treatment with placebo (one-sided $p=0.0003$). CDI recurrence rates were 15.7% and 25.7% in the bezlotoxumab and placebo groups, respectively [−9.9 (95% CI: −15.5, −4.3)]. CDI recurrence rate in the actoxumab/bezlotoxumab group was 14.9% and was significantly (one sided $p<0.0001$) better than placebo, but was not significantly better than bezlotoxumab ($p=0.3718$). Consistent with PN001, reduction in CDI recurrence rate for the bezlotoxumab group versus placebo was observed in all pre-specified subgroups of subjects. Bezlotoxumab demonstrated superiority over placebo with respect to the key secondary endpoint of global cure (66.8% in the bezlotoxumab and 52.1% in the placebo group; one-sided $p<0.0001$ [14.6 (95% CI: 7.7, 21.4)]. In comparing actoxumab/bezlotoxumab to bezlotoxumab alone with respect to achieving global cure, the planned one-sided p-value designed to demonstrate actoxumab/bezlotoxumab was superior to bezlotoxumab was 0.9969 and the one-sided p-value to evaluate if bezlotoxumab was superior to actoxumab/bezlotoxumab was 0.0031.

As per the Integrated Statistical Analysis Plan (ISAP), the data from the two Phase 3 trials were pooled to provide integrated statistical analyses of efficacy and safety. From the pooled dataset (PN001+PN002), the CDI recurrence rates were 16.5% for bezlotoxumab and 26.6% for placebo; the adjusted difference in CDI recurrence rates between the bezlotoxumab and the placebo groups was 10.0% (95% CI: −14.0% to −6.0%, one-sided $p<0.0001$) (shown in FIG. 2).

In pre-specified subgroups of subjects (i.e., patients ≥65 years of age, with a history of CDI in the past 6 months before the baseline episode, clinically severe CDI, 027 ribotype, epidemic strain or compromised immunity), bezlotoxumab reduced CDI recurrence rates compared to placebo (FIG. 3).

For example, CDI recurrence rates among patients ≥65 years of age in the bezlotoxumab group was 15.4% versus 31.4% in the placebo group (difference −16.0 [95% CI, −21.7, −10.2]). Among patients with a history of CDI in the past 6 months before the baseline episode, the CDI recurrence rate was 25.0% in the bezlotoxumab group versus 41.1% in the placebo group (difference −16.1 [95% CI, −24.7, −7.3]). The results from the pooled dataset for the secondary endpoint of global cure provide strong supportive evidence that treatment with bezlotoxumab significantly increases the proportion of subjects who achieve global cure over a period of 12 weeks as compared to placebo. The global cure rates were 63.5% for bezlotoxumab and 53.7% for placebo; the estimated adjusted difference between the bezlotoxumab group and the placebo group was 9.7% (95% CI: 4.8% to 14.5%, one-sided $p<0.0001$).

In conclusion, the Phase 3 trials demonstrated that in patients receiving standard of care for CDI, treatment with bezlotoxumab was superior to placebo in prevention of CDI recurrence (primary endpoint) over a period of 12 weeks. In both Phase 3 trials, bezlotoxumab was efficacious in the trial population overall, as well as in all subgroups of patients that are considered at high risk for CDI recurrence and/or CDI-related adverse outcomes. Superior efficacy of bezlotoxumab alone compared to placebo was also demonstrated for the secondary endpoint, global cure, in PN002 and in the pooled PN001+PN002 dataset. Bezlotoxumab was well tolerated and had a safety profile similar to placebo.

Example 2

Genome-Wide Association Study to Identify SNP's Associated with Response to Treatment Comprising a TcdB Antibody and an Antibiotic A genome wide association study was performed to assess whether genetic variants across the human genome associated with a treatment difference across patients randomized to the different arms of the studies. Because analysis of clinical studies demonstrated that therapeutic benefit was primarily derived for bezlotoxumab and not from actoxumab subjects from the treatment arms containing bezlotoxumab (bezlotoxumab alone and bezlotoxumab+actoxumab) were pooled and compared to placebo (no administration of monoclonal antibodies just 0.9% NaCl). The pooled data set for the GWAS analysis was based on approximately 897 patients from both MODIFY I and II (PN001 and PN002, also referred to herein as "PGx dataset"). The subjects from the actoxumab arm alone were not used in the GWAS analysis. Only subjects who appropriately consented to the genetic analysis were included in the GWAS analysis. A summary of subjects that were used in the GWAS analyses and the CDI recurrence rate in each of the subject groups is provided in FIG. 4.

Genotype and Clinical Data

DNA was extracted from peripheral blood of consenting subjects using standard procedures. Genetic data was generated from DNA samples using the UK Biobank Axiom® Array (Affymetrix, Santa Clara) and manufacturers recommended reagents and conditions. The array interrogates approximately 800,000 polymorphic sites across the genome. Appropriate genetic quality control procedures and imputation methods were applied to the data sets.

Example 3

Statistical Methods

Two pivotal studies MODIFY I and II (PN001 and PN002) were conducted to evaluate bezlotoxumab (MK-6072), actoxumab (MK-3415), a combination of bezlotoxumab and actoxumab (MK-3415A), and placebo for the prevention of *C. difficile* recurrence (rCDI) in patients on standard of care antibiotics. The primary clinical endpoint of interest was rCDI, defined as a development of a new episode of diarrhea (3 or more loose stools in 24 or fewer hours) associated with a positive local or central lab stool test for toxigenic *C. difficile* following clinical cure of the initial CDI episode. The primary efficacy endpoint was the proportion of patients with CDI recurrence assessed through week 12. The initial efficacy results from the two studies showed that bezlotoxumab was superior to placebo in reducing the CDI recurrence rate (p<0.0001) and actoxumab alone did not demonstrate efficacy compared to placebo (p=0.3182).

Genetic data were generated on a commercial Affymetrix Axiom® platform using the UK Biobank array. The Axiom array has approximately 836,000 genetic variants. Genotype imputation on genotyped samples from both PN001 and PN002 studies using the 1000 Genomes Phase 3 reference data and Impute2 software (Howie et al., Fast and accurate genotype imputation in genome-wide association studies through pre-phasing. *Nature Genetics* 44(8): 955-959 (2012)) were performed after genetic quality control (QC) but prior to the genetic analysis. The primary genetic variant set used as input to the analyses described below included both assayed and imputed SNPs. Study objectives were to conduct a genome-wide single variant analysis to identify genetic variation that associates with treatment response as defined by a decreased risk of CDI recurrence.

Genetic principal components (PCs) were calculated using EIGENSOFT (Price et al. (2006) Principal components analysis corrects for stratification in genome-wide association studies. Nat Genet 38: 904-909), and the first five PCs were used as covariates in the statistical models to control for confounding due to population stratification in the samples, which included patients from multiple race groups. For analysis of CDI recurrence endpoint, the likelihood ratio test (LRT) based logistic regression was used to assess the combined prognostic and treatment-related association of each genetic variant to response. Relevant covariates including the top 5 PCs and HOSPSTR (Hospitalization Flag, Inpatient or Outpatient) and SOCSTR (standard of Care (SOC) Flag, Fidaxomicin, Metronidazole or Vancomycin) were included in the models and the genotypes were coded to detect additive genetic effects. Within each genetic variant, genotype was numerically coded for an individual patient as 0, 1 or 2 depending on the number of copies of the minor allele. Treatment was numerically recoded as 0, 1 and 2 depending on whether a patient received Placebo+SOC therapy, monotherapy (actotoxumab or bezlotoxumab alone, MK-3415 or MK-6072 respectively)+SOC therapy, or combination therapy (actotoxumab+bezlotoxumab MK-3415A)+SOC therapy, respectively in terms of the test or comparison. The full model was:

$$\log it(p_{ij}) = \beta_0 + HOSPSTR + SOCSTR + PC1 + PC2 + PC3 + PC4 + PC5 + \beta_1 \times trt_i \beta_2 \times g_j + \beta_3 \times trt_i \times g_j$$

where $p_{ij}$ is the CDI recurrence rate for treatment group i and genotype j.

The comparative model was:

$$\log it(p_{ij}) = \beta^*_0 + HOSPSTR + SOCSTR + PC1 + PC2 + PC3 + PC4 + PC5 + \beta^*_1 \times trt_i$$

The difference in $-2 \times \log(LR)$ was compared to a chi-square distribution with 2 degrees of freedom. Due to limited power in SNPs with low MAF, only common SNPs with minor allele frequency (MAF)≥0.01 were tested in this analysis. Bonferroni was used for multiplicity adjustment. Criterion of p-value threshold 5E-8 was used to declare statistical significance, which means SNPs with p-values less than the 5E-8 would be considered genome-wide statistically significant.

In addition to the traditional GWAS analysis, HLA association analyses in the xMHC (extended Major Histocompatibility Complex) were conducted. The HLA alleles in three Class I loci (HLA-A, HLA-B and HLA-C) and four class II loci (HLA-DRB1, HLA-DQA1, HLA-DQB1 and HLA-DPB1) were imputed using HIBAG (Zheng, et al. HIBAG-HLA Genotype Imputation with Attribute Bagging, *The Pharmacogenomics Journal*, doi: 10.1038/tpj.2013.18).

The best-guess imputed HLA types were used by setting the call rate threshold to 0.5, meaning that the imputed genotypes were set as missing if their imputation posterior probability was less than 0.5. The multi-allelic HLA types were converted to the bi-allelic HLA alleles for each unique HLA allele. The bi-allelic HLA alleles were then recoded as 0, 1 and 2 in terms of the number of their minor allele carriers by assuming an additive genetic model. For example, if an HLA allele is HLA-A*11:01, its genotypes X/X, HLA-A*11:01/X and HLA-A*11:01/HLA-A*11:01 would be assigned as 0, 1 and 2 respectively. Totally 219 HLA alleles from three class I and four class II HLA genes were imputed via HIBAG, out of which 112 were common with MAF >1% and used for analysis. The statistical analysis method for HLA alleles was exactly the same as that described above for GWAS SNPs. Bonferroni was used for multiplicity adjustment and the statistically significant p-value threshold was set as 4.46E-04 (0.05/112) for HLA association analysis.

Example 4

Figure 6:
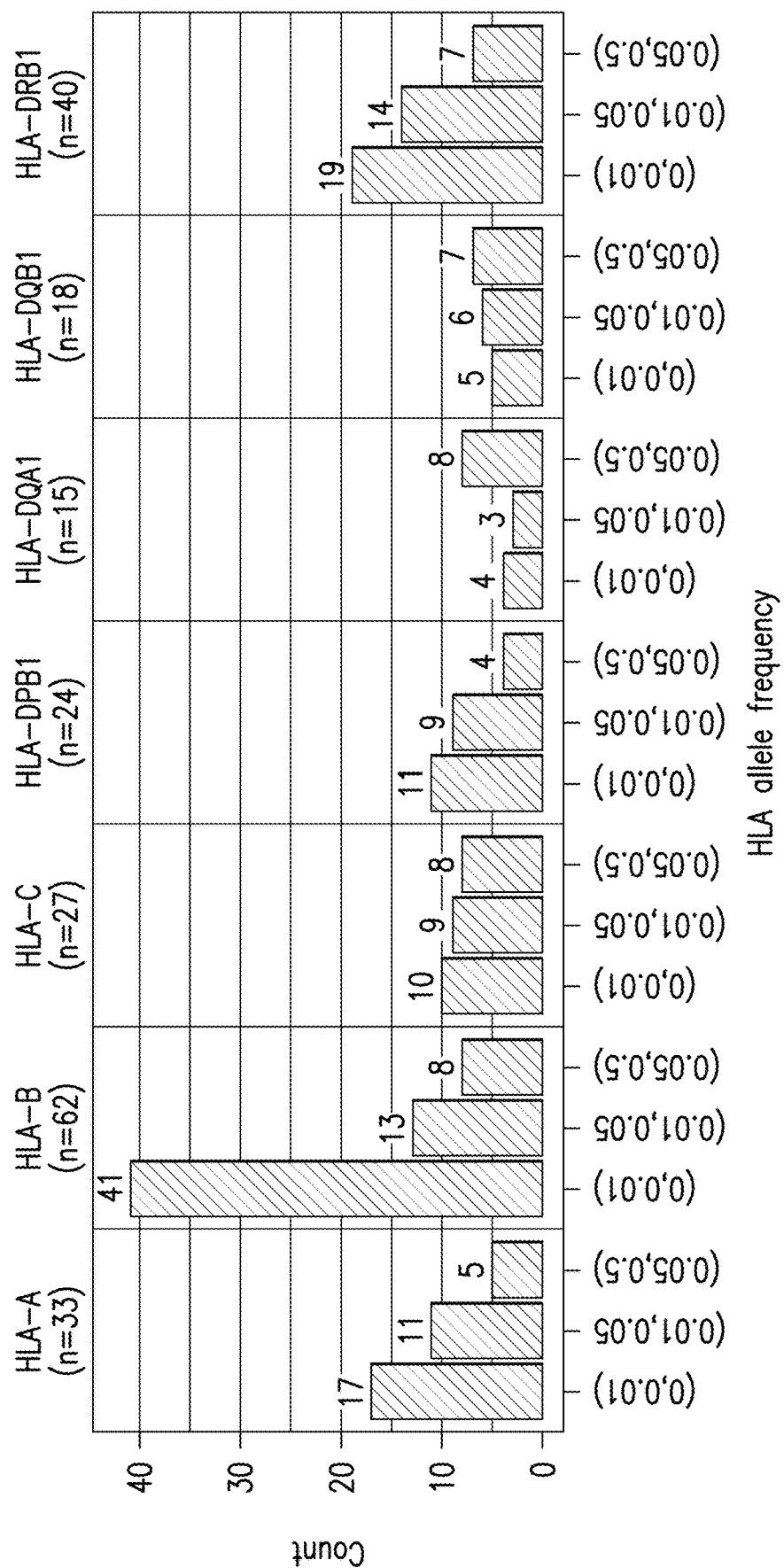
FIG. 6 illustrates imputed HLA data from GWAS data in xMHC pooled from PN001 and PN002 (N=1001). 219 HLA alleles were imputed in the 3 class 1 and 4 class II HLA genes, in which 112 were common with a minor allele frequency ("MAF")>0.01.

Evaluation of the GWAS Results to CDI Recurrence when Comparing Bezlotoxumab Containing Arms to Placebo The original GWAS data were QCed and further imputed using Impute2 software. For subjects filtering, subjects with genotypes ≤97% of loci, problematic gender check (F>0.8 called as male, F<0.2 called as female), duplicates or at least 2nd degree relatives via checking all the pairwise IBD (Identity by Descent) values and large Heterozygosity (≥3 standard deviations from the mean) were removed. For SNP filtering (after sample filtering), SNPs with call rates ≤97% and non-autosomal SNPs were removed. After QC and imputation, there were 1,001 subjects and 7,570,264 variants available for analysis. The 104 subjects who received actoxumab alone were further removed in the analysis since actoxumab did not demonstrate efficacy compared to placebo (p=0.3182). By definition, those with rCDI must initially reach clinical cure (defined as ≤14 days of SOC therapy and no diarrhea (≤2 loose stools per 24 hours) for 2 consecutive days following completion of SOC therapy for the initial CDI episode), and therefore those 193 patients who did not have an initial clinical cure were not included in the analyses. The MAF or HLA allele frequency distributions of the imputed HLA data from GWAS data in xMHC pooled from both PN001 and PN002 (N=1,001) were visualized in FIG. 6.

Figure 7:
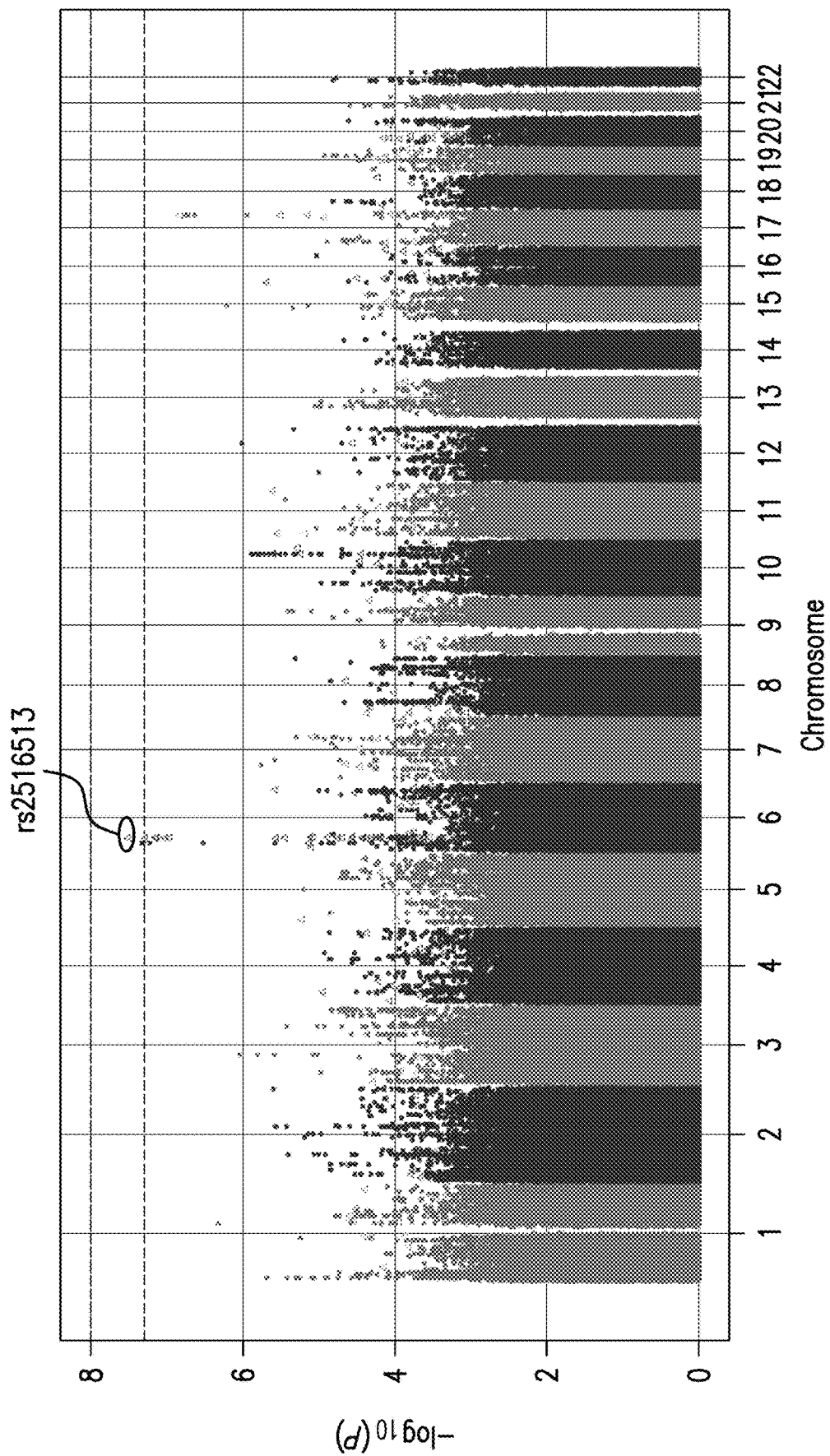
FIG. 7 illustrates a "Manhattan plot" that identifies the p-values of genetic variants associated with treatment response and CDI recurrence rate.
Figure 8:
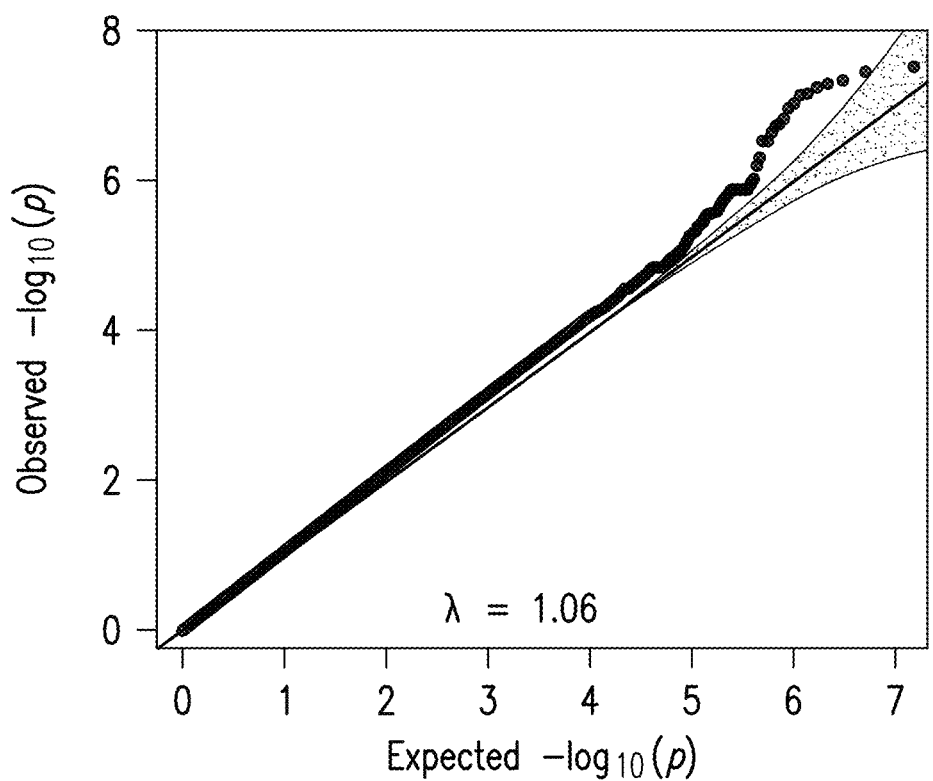
FIG. 8 illustrates a QQ plot of recurrent CDI GWAS analysis.
Figure 9:
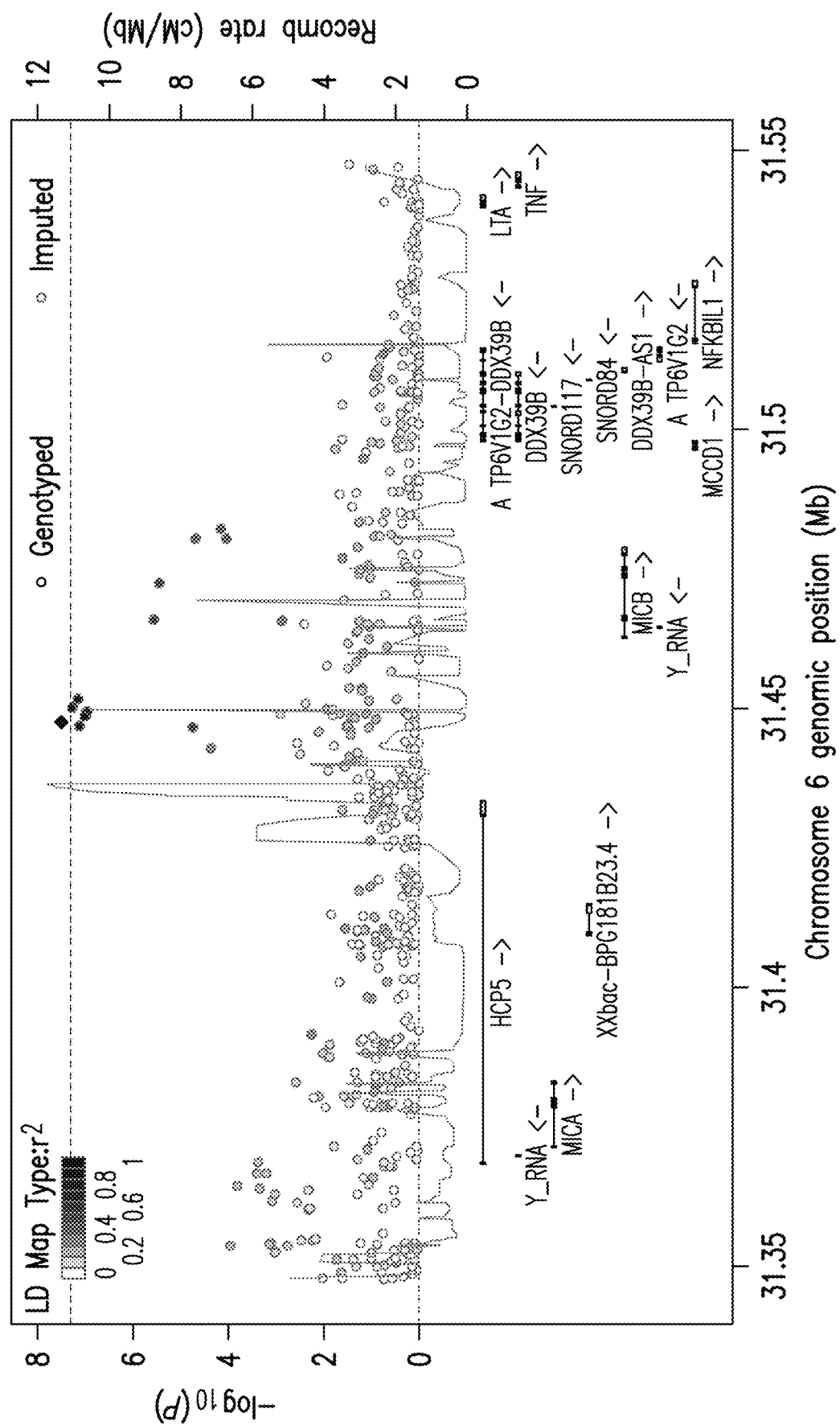
FIG. 9 illustrates the regional plot of p-values of genetic variants near rs2516513 showing association with treatment response and CDI recurrence. The diamond-shaped point represents the target SNP rs2516513. The grey scale represents the LD information of SNPs in relation to rs11209026. The curve represents the recombination rate (cM/Mb as per HapMap data).

The genome-wide association results were summarized in a Manhattan plot (FIG. 7) and a QQ-plot (FIG. 8). Three SNPs were identified from the GWAS analysis to be associated with the rCDI endpoint, in which rs2516513 (6: 31447588) was located in the xMHC and rs113379306 (6:17333351) and rs76166871 (6:17329940) were located outside of, but near the xMHC. In addition, the HLA association analyses identified three HLA alleles associated with the rCDI endpoint as well. The detailed association results of these six markers are summarized in Table 3. Similar results were obtained when analyzing the GWAS data while including the patients who did not reach clinical cure as a sensitivity analysis and the subset data with patients of European ancestry (results not shown). A regional plot of rs2516513 is shown in FIG. 9.

TABLE 3

GWAS and HLA association results.[1, 2]

| SNP/HLA allele | Pos | A1 | A2 | Imp. | N | MAF | P | Conseqence |
|---|---|---|---|---|---|---|---|---|
| rs2516513 | 31447588 | T | C | N | 701 | 0.23 | 3.04E−08 | Intergenic, downstream |
| rs113379306 | 17333351 | A | C | Y | 704 | 0.04 | 3.54E−08 | Intergenic |
| rs76166871 | 17329940 | A | G | Y | 704 | 0.04 | 4.64E−08 | Intergenic |
| HLA-DRB1*07:01 | | DRB1*07:01 | X | Y | 689 | 0.10 | 1.93E−05 | |
| HLA-DQB1*02:02 | | DQB1*02:02 | X | Y | 699 | 0.08 | 1.30E−04 | |
| HLA-DQA1*02:01 | | DQA1*02:01 | X | Y | 699 | 0.11 | 5.18E−05 | |

[1]All SNP's HLA alleles are on human chromosome 6.

[2]The clinical endpoint for all data was rCDI.

Additional conditional analyses were conducted to identify relatively independent signals for the six SNPs and HLA alleles. Table 4 provides pairwise linkage disequilibrium (LD) information of statistically significant SNPs and HLA alleles from the GWAS and HLA association analyses for the six markers. The rs76166871 and rs113379306 SNPs were almost in perfect LD with each other (LD $r^2=0.99$) and HLA-DRB1*07:01 and HLA-DQA1*02:01 were almost in perfect LD with each other (LD $r^2=0.98$), whereas the rs2516513 and rs113379306 SNPs were totally independent of each other (LD $r^2=0$). The HLA-DRB1*07:01 and HLA-DQB1*02:02 alleles were in moderate LD (LD $r^2=0.68$). The only unique statistically significant finding from the conditional analysis was the rs2516513 SNP based on the GWAS results since the p-value of rs76166871 was not significant (p>0.05) when conditioning on rs2516513. HLA-DRB1*07: 01 and HLA-DQB1*02:02 have an LD correlation $r^2$ of 0.68 and HLA-DRB1*07:01 is more significant in single marker analysis. In addition, HLA-DRB1*07:01 could explain more variation than HLA-DQB1*02:02 when combined with rs2516513. The conditional analysis results between the top two signals rs2516513 and HLA-DRB1*07:01 are shown in Table 5, which indicates they were relatively independent of each other.

TABLE 4

Linkage disequilibrium of SNPs and HLA alleles from GWAS and HLA association analyses.

| CHR_A | BP_A | SNP_A | CHR_B | BP_B | SNP_B | LD r² |
|---|---|---|---|---|---|---|
| 6 | 31447588 | rs2516513 | 6 | 17333351 | rs113379306 | 0 |
| 6 | 17329940 | rs76166871 | 6 | 17333351 | rs113379306 | 0.99 |
| 6 | 31447588 | rs2516513 | 6 | 17329940 | rs76166871 | 0 |
| 6 | 31447588 | rs2516513 | 6 | 32571419 | HLA-DRB1*07:01 | 0.14 |
| 6 | 17329940 | rs76166871 | 6 | 32571419 | HLA-DRB1*07:01 | 0 |
| 6 | 32571419 | HLA-DRB1*07:01 | 6 | 32637621 | HLA-DQA1*02:01 | 0.98 |
| 6 | 32571419 | HLA-DRB1*07:01 | 6 | 32663925 | HLA-DQB1*02:02 | 0.68 |
| 6 | 32637621 | HLA-DQA1*02:01 | 6 | 32663925 | HLA-DQB1*02:02 | 0.66 |

TABLE 5

Conditional analysis results from the top GWAS and HLA markers associated with rCDI.

| Condition on | Test of | p-value |
|---|---|---|
| HLA-DRB1*07:01 | rs2516513 | 5.70E−05 |
| rs2516513 | HLA-DRB1*07:01 | 1.40E−02 |

An SNP association region plot of rs2516513 (6:31447588, assayed) in the xMHC region is shown in FIG. 9. rs2516513 is an intergenic and downstream variant near the HCPS gene. Several SNPs around the rs2516513 SNP also showed association with the rCDI endpoint, but mainly due to their high LD with this SNP. The genetic effects are summarized in Table 6 and Table 7 for the rs2516513 and HLA-DRB1*07:01 markers, respectively. The risk difference ((bezlotoxumab+(combined bezlotoxumab/actoxumab))−placebo) of developing rCDI in the sub-population of T-carriers is −21.50%, which is about twice the rate from the overall population (−10.70%). Similarly, the risk difference of developing rCDI in the sub-population of HLA-DRB1*07:01-carriers is −32.30%, which is about three times the rate from the overall population (−10.70%). These results demonstrate the relevance of the markers identified from the GWAS and HLA association analyses to predict subjects who have improved benefit from bezlotoxumab treatment. In addition the combination of SNPs and HLA alleles can also provide utility in predicting subjects who have improved benefit from bezlotoxumab treatment. As an example, Table 8 shows the genetic effects of subjects who either carry either the rs2516513 T allele or the HLA-DRB1*07:01 allele, as well as subjects who carry both the rs2516513 T allele and the HLA-DRB1*07:01 allele.

TABLE 6

Summary of rs2516513 genotype subgroups.

| | CDI Recurrence | | | | |
|---|---|---|---|---|---|
| Genotype {population rel. freq.} | C_C {.59} | T_C {.35} | T_T {.06} | T_C or T_T {.41} | Overall |
| BEZ and ACT + BEZ | 31.80% (87/274) | 12.70% (20/157) | 3.30% (1/30) | 11.20% (21/187) | 23.40% (108/461) |
| Placebo | 35.30% (48/136) | 32.20% (29/90) | 35.70% (5/14) | 32.70% (34/104) | 34.20% (82/240) |
| Risk Difference | −3.50% | −19.50% | −32.40% | −21.50% | −10.70% |
| Relative Risk | 0.9 | 0.4 | 0.09 | 0.34 | 0.69 |

Risk Difference = MK − P
Relative Risk = MK:P
Note:
59% SNP− (C_C) and 41% SNP+ (T_C or T_T) in phase III studies (P001 + P002, Clinical Cure = Yes)

TABLE 7

Summary of HLA-DRB1*07:01 genotype.

| | CDI Recurrence | | | | |
|---|---|---|---|---|---|
| Genotype {population rel. freq.} | X:X {.81} | 0701:X {.18} | 0701:0701 {.01} | 0701:X or 0701:0701 {.19} | Overall |
| BEZ and ACT + BEZ | 27.30% (101/370) | 6.40% (5/78) | 0.00% (0/5) | 6.00% (5/83) | 23.40% (106/453) |
| Placebo | 32.80% (62/189) | 38.60% (17/44) | 33.30% (1/3) | 38.30% (18/47) | 33.90% (80/236) |

TABLE 7-continued

Summary of HLA-DRB1*07:01 genotype.

| Genotype {population rel. freq.} | CDI Recurrence | | | | |
|---|---|---|---|---|---|
| | X:X {.81} | 0701:X {.18} | 0701:0701 {.01} | 0701:X or 0701:0701 {.19} | Overall |
| Risk Difference | −5.50% | −32.20% | −33.30% | −32.30% | −10.50% |
| Relative Risk | 0.83 | 0.27 | 0 | 0.16 | 0.69 |

Risk Difference = MK − P
Relative Risk = MK:P
Note:
81% allele - (X:X) and 19% allele (HLA-DRB1*07:01:X or HLA-DRB1*07:01:HLA-DRB1*07:01) in phase III studies (PN001 + PN002, Clinical Cure = Yes)

TABLE 8

Summary of HLA-DRB1*07:01 and/or rs2516513 genotype subgroups.

| Genotype→ {population rel. freq.} | CDI Recurrence | | | CDI Recurrence |
|---|---|---|---|---|
| | C_C or XX {.55} | T_C or T_T or 0701:X or 0701:0701 {.45} | Overall | (T_C or T_T) & (0701:X or 0701:0701) N = 102 |
| BEZ and ACT + BEZ | 33.1% (86/120) | 11.3% (23/204) | 23.5% (109/464) | 4.5% (3/66) |
| Placebo | 32.0% (40/125) | 36.5% (42/115) | 34.2% (82/240) | 27.8% (10/36) |
| Risk Difference | 1.1% | −25.2% | −10.7% | −23.2% |
| Relative Risk | 1.03 | 0.31 | 0.69 | 0.16 |

Risk Difference = MK − P
Relative Risk = MK:P
Note:
55% C_C or XX and 45% T_C or T_T or 0701:X or 0701:0701 in phase III studies (P001 + P002)

Example 5 rCDI Stratified by Genotype and Risk Category rCDI rates for the PGx population were compared to subgroups at high/low risk for rCDI stratified by SNP rs2516513. High risk for rCDI was defined as having one or more of the following six factors: history of one or more episodes of CDI in the past six months, sever CDI at baseline (per Zar score), age ≥65 years, CDI caused by a hypervirulent strain (027, 078 or 244 ribotypes), immunocompromised, or received concomitant systemic antibiotics. Low risk for rCDI was defined as not having any of the high risk factors for rCDI.

Figure 10A:
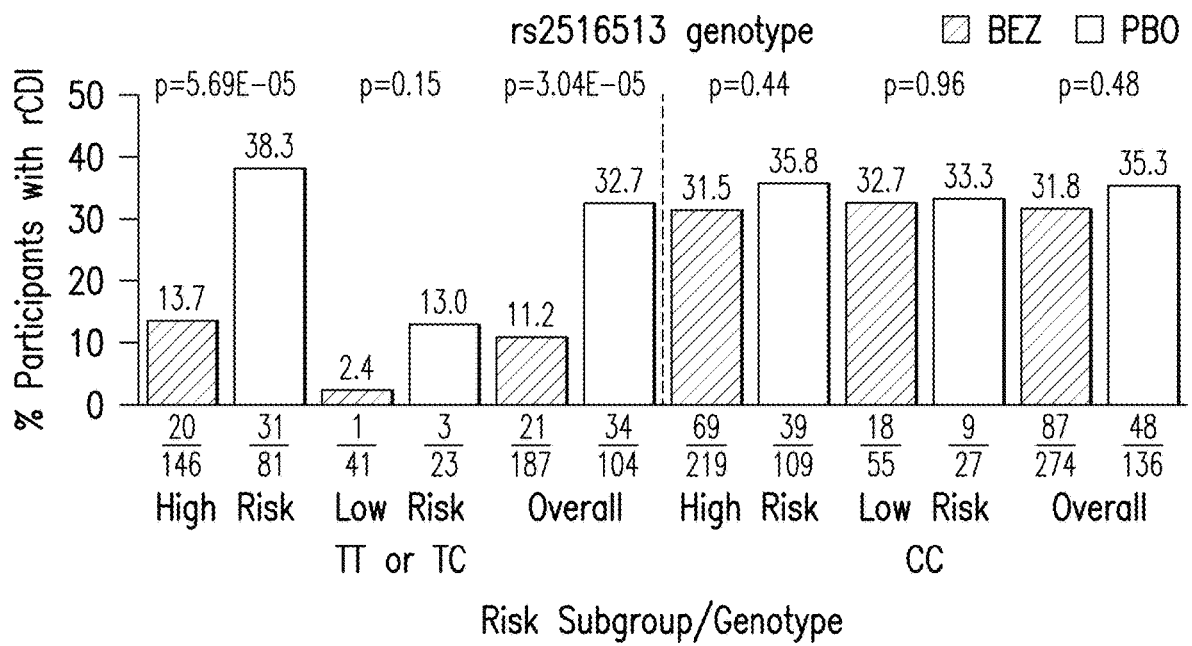
FIG. 10. rCDI Stratified by Genotype and Risk Category.
Figure 10B:
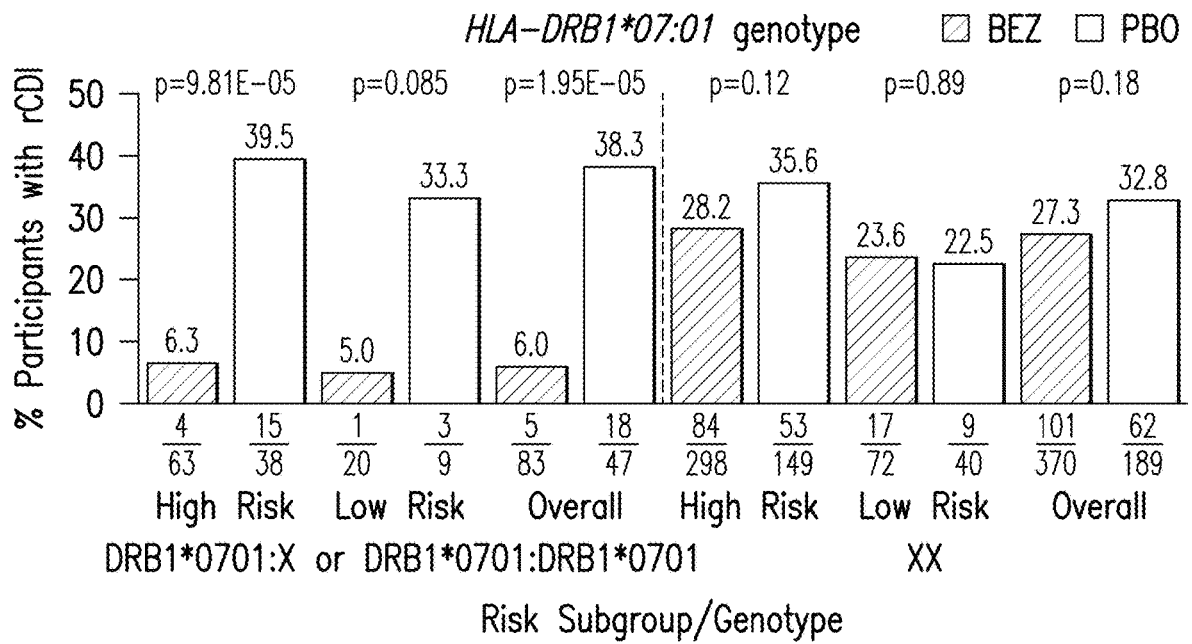

A significant reduction in the rate of rCDI occurred in Bezlotoxumab ("BEZ")-treated participants who carried the T allele of rs2516513 (−21.5% risk difference with p-value=3.04E-05 versus −10.7% risk difference overall without genotype stratification) and the HLA-DRB1*07:01 allele (−32.3% risk difference with p-value=1.95E-05 versus −10.5% risk difference overall without genotype stratification) compared with PBO recipients (see FIG. 10). The effect sizes of the T and HLA-DRB1*07:01 alleles were more prominent in BEZ-treated participants at high risk of rCDI (−24.6% risk difference versus PBO, p-value=5.69E-05; and −33.2% risk difference versus PBO, p-value=9.81E-05, respectively). In CC homozygous patients, rCDI rates were similar in both treatment groups and in patients at high and low risk of rCDI.

The trends in the effect of these alleles were also observed in participants in the low risk subgroups, although they were not statistically significant (T allele: −10.6% risk difference versus PBO, p-value=0.15; and HLA-DRB1*07:01 allele: −28.3% risk difference versus PBO, p-value=0.085), which could be due to the low number of participants in these subgroups.

Figure 11A:
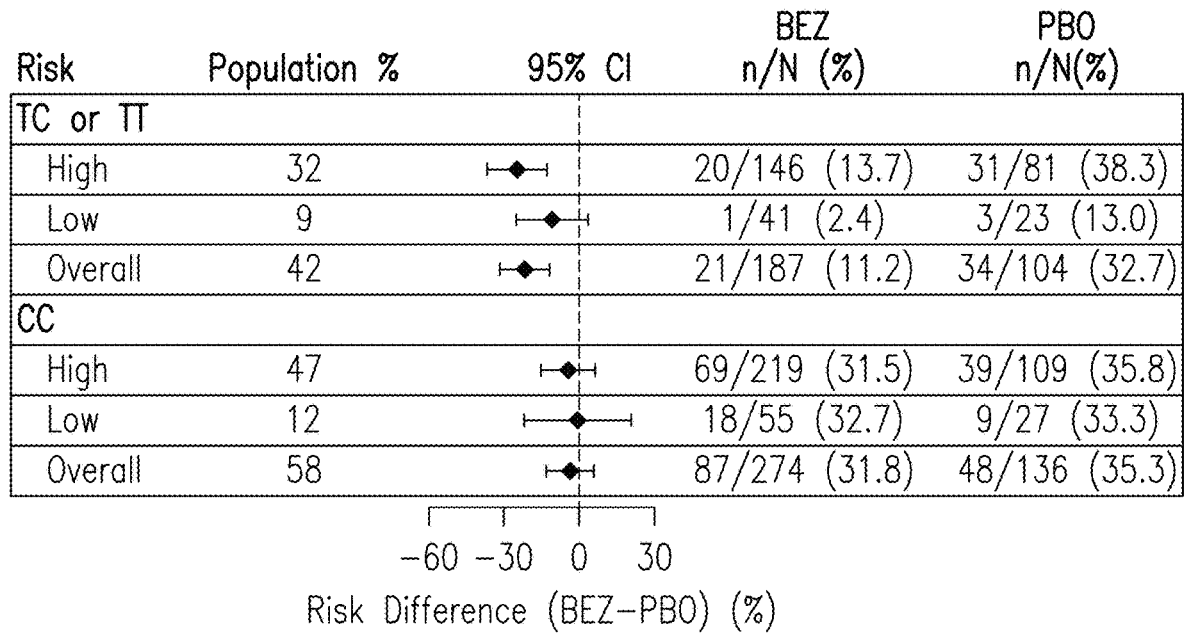
FIG. 11. rCDI Stratified by Genotypes and the rCDI Risk Categories.
Figure 11B:
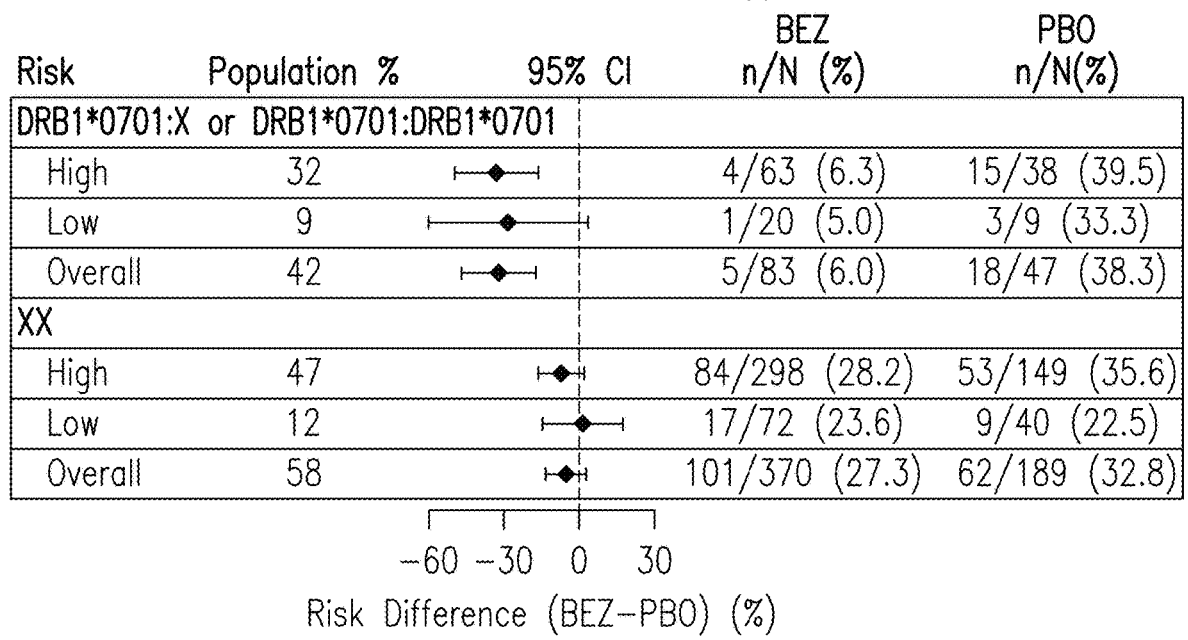

FIG. 11 shows that the reduction in risk of rCDI in BEZ-treated participants carrying the T allele of rs2516513 and HLA-DRB1*07:01 compared with PBO recipients varied according to risk factors. Results from the rs2516513 genotype indicate that participants carrying the T allele exhibited a strong trend for benefit of BEZ treatment, regardless of the rCDI risk categories; whereas 47% of participants carrying the CC genotype who were at high risk for rCDI had limited benefit from BEZ treatment. High risk participants with the HLA-DRB1*07:01 genotype benefited from BEZ treatment regardless of genetic stratification, although the association is not statistically significant in the low risk subgroup (p-value=0.085). Within the low risk subgroups, approximately 9% of participants carrying the T allele and approximately 4% carrying the HLA-DRB1*07: 01 allele may have benefited from BEZ treatment.

What is claimed:

1. A method of preventing the recurrence of a *Clostridium difficile* (*C. difficile*) infection comprising:
administering a therapeutically effective amount of bezlotoxumab that targets *C. difficile* toxin B (TcdB treatment) to a patient in need thereof,
wherein said patient, prior to the administration of the TcdB treatment, has tested positive for at least one copy of a better response allele from one or more TcdB treatment response markers, wherein the better response allele from one or more TcdB treatment response marker is selected from the group consisting of:
a) the T allele of the rs2516513 single nucleotide polymorphism (SNP);
b) the A allele of the rs113379306 SNP;
c) the A allele of the rs76166871 SNP;
d) the HLA-DRB1*07:01 allele of the HLA-DRB1 gene;
e) the HLA-DQB1*02:02 allele of the HLA-DQB1 gene;
f) the HLA-DQA1*02:01 allele of the HLA-DQA1 gene; and
g) a linked variant having a linkage disequilibrium $r^2$ value of at least 0.75 to one or more of the TcdB treatment response markers set forth in a)-f).

2. The method of claim 1, wherein said patient, prior to the administration of bezlotoxumab, has tested positive for at least one copy of the T allele of the rs2516513 SNP or the HLA-DRB1*07:01 allele of the HLA-DRB1 gene.

3. The method of claim 2, wherein said patient, prior to the administration of bezlotoxumab, has tested positive for at least one copy of the T allele of the rs2516513 SNP and the HLA-DRB1*07:01 allele of the HLA-DRB1 gene.

4. The method of claim 1, wherein the method further comprises treating said patient with an antibiotic that is effective against *C. difficile* infection.

5. The method of claim 4, wherein the antibiotic is selected from the group consisting of vancomycin, metronidazole, and fidaxomicin.

6. A method of determining if a patient is likely to respond to a medicament that targets *C. difficile* toxin B (TcdB) in a human patient, said method comprising:
(a) obtaining or having obtained a biological sample from said patient;
(b) determining whether a better response allele of at least one TcdB treatment response marker is present in the biological sample, wherein the better response allele of at least one TcdB treatment response marker is selected from the group consisting of:
i. the T allele of the rs2516513 single nucleotide polymorphism (SNP);
ii. the A allele of the rs113379306 SNP;
iii. the A allele of the rs76166871 SNP;
iv. the HLA-DRB1*07:01 allele of the HLA-DRB1 gene;
v. the HLA-DQB1*02:02 allele of the HLA-DQB1 gene;
vi. the HLA-DQA1*02:01 allele of the HLA-DQA1 gene; and
vii. a linked variant having a linkage disequilibrium $r^2$ value of at least 0.75 to one or more of the TcdB treatment response markers set forth in i)-vi); and
(c) diagnosing the patient as susceptible to treatment with a TcdB medicament when the presence of the better response allele in the biological sample is detected.

7. The method of claim 6, further comprising step (d), which comprises administering a therapeutically effective amount of the TcdB medicament to the diagnosed patient.

8. The method of claim 7, wherein the TcdB medicament is a TcdB antibody or antigen binding fragment thereof.

9. The method of claim 8, wherein step (d) further comprises administering an antibiotic that is effective against *Clostridium difficile* infection to the patient.

10. The method of claim 9, wherein the antibiotic is selected from the group consisting of vancomycin, metronidazole, and fidaxomicin.

11. The method of claim 8, wherein in step (b), the T allele of the rs2516513 SNP or the HLA-DRB1*07:01 allele of the HLA-DRB1 gene is detected, and in step (c), the patient is diagnosed as susceptible to treatment with a TcdB antibody when the T allele of the rs2516513 SNP or the HLA-DRB1*07:01 allele of the HLA-DRB1 gene is detected or if both the rs2516513 SNP and the HLA-DRB1*07:01 allele of the HLA-DRB1 gene are detected.

12. The method of claim 11, wherein the TcdB antibody is bezlotoxumab.

13. The method of claim 12, wherein the patient is a human who has been diagnosed with a *Clostridium difficile* infection, or exhibits symptoms of *Clostridium-difficile* associated disease.

14. The method of claim 13, wherein step (b) comprises sending the biological sample to a diagnostic laboratory to determine if a better response allele of the TcdB treatment response marker is present in the sample.

15. The method of claim 14, wherein the patient is at high-risk for recurrent CDI.

16. A kit for testing a patient for the presence or absence of at least one copy of a better response allele of one or more TcdB treatment response markers selected from the group consisting of:
   a) the T allele of the rs2516513 single nucleotide polymorphism (SNP);
   b) the A allele of the rs113379306 SNP;
   c) the A allele of the rs76166871 SNP;
   d) the HLA-DRB1*07:01 allele of the HLA-DRB1 gene;
   e) the HLA-DQB1*02:02 allele of the HLA-DQB1 gene;
   f) the HLA-DQA1*02:01 allele of the HLA-DQA1 gene; and
   g) a linked variant having a linkage disequilibrium $r^2$ value of at least 0.75 to the TcdB treatment response marker set forth in a)-f),
wherein the kit comprises a set of oligonucleotides designed to genotype at least one of the TcdB treatment response markers.

17. The kit of claim 16, wherein the TcdB treatment response marker is the rs2516513 SNP.

18. The kit of claim 16, wherein the oligonucleotides are allele specific oligonucleotide probes.

19. The method of claim 1, wherein said linked variant has a linkage disequilibrium $r^2$ value of at least 0.85.

20. The method of claim 1, wherein said linked variant has a linkage disequilibrium $r^2$ value of at least 0.90.

21. The method of claim 1, wherein said linked variant has a linkage disequilibrium $r^2$ value of at least 0.95.

22. The method of claim 1, wherein said one or more TcdB treatment response marker is selected from the group consisting of:
   a) the T allele of the rs2516513 single nucleotide polymorphism (SNP);
   b) the A allele of the rs113379306 SNP;
   c) the A allele of the rs76166871 SNP;
   d) the HLA-DRB1*07:01 allele of the HLA-DRB1 gene;
   e) the HLA-DQB1*02:02 allele of the HLA-DQB1 gene; and
   f) the HLA-DQA1*02:01 allele of the HLA-DQA1 gene.

23. The method of claim 5, wherein said linked variant has a linkage disequilibrium $r^2$ value of at least 0.85.

24. The method of claim 5, wherein said linked variant has a linkage disequilibrium $r^2$ value of at least 0.90.

25. The method of claim 5, wherein said linked variant has a linkage disequilibrium $r^2$ value of at least 0.95.

26. The method of claim 5, wherein said one or more TcdB treatment response marker is selected from the group consisting of:
   a) the T allele of the rs2516513 single nucleotide polymorphism (SNP);
   b) the A allele of the rs113379306 SNP;
   c) the A allele of the rs76166871 SNP;
   d) the HLA-DRB1*07:01 allele of the HLA-DRB1 gene;
   e) the HLA-DQB1*02:02 allele of the HLA-DQB1 gene; and
   f) the HLA-DQA1*02:01 allele of the HLA-DQA1 gene.

27. The kit of claim 16, wherein said linked variant has a linkage disequilibrium $r^2$ value of at least 0.85.

28. The kit of claim 16, wherein said linked variant has a linkage disequilibrium $r^2$ value of at least 0.90.

29. The kit of claim 16, wherein said linked variant has a linkage disequilibrium $r^2$ value of at least 0.95.

30. The kit of claim 16, wherein said one or more TcdB treatment response marker is selected from the group consisting of:
   a) the T allele of the rs2516513 single nucleotide polymorphism (SNP);
   b) the A allele of the rs113379306 SNP;
   c) the A allele of the rs76166871 SNP;
   d) the HLA-DRB1*07:01 allele of the HLA-DRB1 gene;
   e) the HLA-DQB1*02:02 allele of the HLA-DQB1 gene; and
   f) the HLA-DQA1*02:01 allele of the HLA-DQA1 gene.

* * * * *

SEQUENCE LISTING

<160> NUMBER OF SEQ ID NOS: 22

<210> SEQ ID NO 1
<211> LENGTH: 108
<212> TYPE: PRT
<213> ORGANISM: Homo sapiens

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Trp Thr Phe Gly Gln Gly Thr Lys Val Glu Ile Lys
            100                 105

<210> SEQ ID NO 2
<211> LENGTH: 11
<212> TYPE: PRT
<213> ORGANISM: Homo sapiens

<400> SEQUENCE: 2

Arg Ala Ser Gln Ser Val Ser Ser Ser Tyr Leu
1               5                   10

<210> SEQ ID NO 3
<211> LENGTH: 7
<212> TYPE: PRT
<213> ORGANISM: Homo sapiens

<400> SEQUENCE: 3

Gly Ala Ser Ser Arg Ala Thr
1               5

<210> SEQ ID NO 4
<211> LENGTH: 9
<212> TYPE: PRT
<213> ORGANISM: Homo sapiens

<400> SEQUENCE: 4

Gln Gln Tyr Gly Ser Ser Thr Trp Thr
1               5

<210> SEQ ID NO 5
<211> LENGTH: 119
<212> TYPE: PRT
<213> ORGANISM: Homo sapiens

<400> SEQUENCE: 5

Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met

```
            35                  40                  45
Gly Ile Phe Tyr Pro Gly Asp Ser Ser Thr Arg Tyr Ser Pro Ser Phe
         50                  55                  60
Gln Gly Gln Val Thr Ile Ser Ala Asp Lys Ser Val Asn Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Arg Arg Asn Trp Gly Asn Ala Phe Asp Ile Trp Gly Gln Gly
                100                 105                 110
Thr Met Val Thr Val Ser Ser
            115

<210> SEQ ID NO 6
<211> LENGTH: 5
<212> TYPE: PRT
<213> ORGANISM: Homo sapiens

<400> SEQUENCE: 6

Ser Tyr Trp Ile Gly
 1               5

<210> SEQ ID NO 7
<211> LENGTH: 17
<212> TYPE: PRT
<213> ORGANISM: Homo sapiens

<400> SEQUENCE: 7

Ile Phe Tyr Pro Gly Asp Ser Ser Thr Arg Tyr Ser Pro Ser Phe Gln
 1               5                  10                  15
Gly

<210> SEQ ID NO 8
<211> LENGTH: 10
<212> TYPE: PRT
<213> ORGANISM: Homo sapiens

<400> SEQUENCE: 8

Arg Arg Asn Trp Gly Asn Ala Phe Asp Ile
 1               5                  10

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Ser Trp
             20                  25                  30
Leu Ala Trp Tyr Gln His Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Asn Ser Phe Pro Trp
                 85                  90                  95
Thr Phe Gly Gln Gly Thr Lys Val Glu Ile Lys
```

<210> SEQ ID NO 10
<211> LENGTH: 11
<212> TYPE: PRT
<213> ORGANISM: Homo sapiens

<400> SEQUENCE: 10

Arg Ala Ser Gln Gly Ile Ser Ser Trp Leu Ala
1               5                   10

<210> SEQ ID NO 11
<211> LENGTH: 7
<212> TYPE: PRT
<213> ORGANISM: Homo sapiens

<400> SEQUENCE: 11

Ala Ala Ser Ser Leu Gln Ser
1               5

<210> SEQ ID NO 12
<211> LENGTH: 9
<212> TYPE: PRT
<213> ORGANISM: Homo sapiens

<400> SEQUENCE: 12

Gln Gln Ala Asn Ser Phe Pro Trp Thr
1               5

<210> SEQ ID NO 13
<211> LENGTH: 122
<212> TYPE: PRT
<213> ORGANISM: Homo sapiens

<400> SEQUENCE: 13

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Asn Tyr
                20                  25                  30

Gly Met His Trp Val Arg Gln Ala Pro Gly Lys Gly Leu Glu Trp Val
            35                  40                  45

Ala Leu Ile Trp Tyr Asp Gly Ser Asn Glu Asp Tyr Thr Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Met Val Arg Val Ile Asp Val Phe Asp Ile Trp
            100                 105                 110

Gly Gln Gly Thr Val Val Thr Val Ser Ser
        115                 120

<210> SEQ ID NO 14
<211> LENGTH: 5
<212> TYPE: PRT
<213> ORGANISM: Homo sapiens

<400> SEQUENCE: 14

Asn Tyr Gly Met His
1               5

```
<210> SEQ ID NO 15
<211> LENGTH: 17
<212> TYPE: PRT
<213> ORGANISM: Homo sapiens

<400> SEQUENCE: 15

Leu Ile Trp Tyr Asp Gly Ser Asn Glu Asp Tyr Thr Asp Ser Val Lys
1               5                   10                  15

Gly

<210> SEQ ID NO 16
<211> LENGTH: 13
<212> TYPE: PRT
<213> ORGANISM: Homo sapiens

<400> SEQUENCE: 16

Trp Gly Met Val Arg Gly Val Ile Asp Val Phe Asp Ile
1               5                   10

<210> SEQ ID NO 17
<211> LENGTH: 32
<212> TYPE: DNA
<213> ORGANISM: Homo sapiens
<220> FEATURE:
<221> NAME/KEY: misc_feature
<222> LOCATION: (16)..(16)
<223> OTHER INFORMATION: N= T or C

<400> SEQUENCE: 17
ttcaaatctc tgctcntcat ttcacaccat ct                           32

<210> SEQ ID NO 18
<211> LENGTH: 33
<212> TYPE: DNA
<213> ORGANISM: Homo sapiens
<220> FEATURE:
<221> NAME/KEY: misc_feature
<222> LOCATION: (17)..(17)
<223> OTHER INFORMATION: N= A or G

<400> SEQUENCE: 18
agatggtgtg aaatgangag cagagatttg aaa                          33

<210> SEQ ID NO 19
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N= A or C

<400> SEQUENCE: 19
tgtctttcaa aactctgatt tgaggnatgt tggacctccc tttctatctt c      51

<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N= T or G

<400> SEQUENCE: 20
gaagatagaa agggaggtcc aacatncctc aaatcagagt tttgaaagac a      51
```

```
<210> SEQ ID NO 21
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N= A or G

<400> SEQUENCE: 21
cgggaggtcg aggctgcagt gagccntcat tgcaccattg cactccagcc t          51

<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: N= T or C

<400> SEQUENCE: 22
aggctggagt gcaatggtgc aatganggct cactgcagcc tcgacctccc g          51
```